United States Patent
De Achaval et al.

(10) Patent No.: US 11,026,905 B2
(45) Date of Patent: Jun. 8, 2021

(54) STAT3 INHIBITORS

(71) Applicants: Tvardi Therapeutics, Inc., Houston, TX (US); Baylor College of Medicine, Houston, TX (US)

(72) Inventors: Sofia De Achaval, Missouri City, TX (US); David John Tweardy, Houston, TX (US)

(73) Assignees: Tvardi Therapeutics, Inc., Houston, TX (US); Baylor College of Medicine, Houston, TX (US)

( * ) Notice: Subject to any disclaimer, the term of this patent is extended or adjusted under 35 U.S.C. 154(b) by 0 days.

(21) Appl. No.: 17/077,821

(22) Filed: Oct. 22, 2020

(65) Prior Publication Data
US 2021/0038544 A1 Feb. 11, 2021

Related U.S. Application Data

(63) Continuation of application No. 17/048,602, filed as application No. PCT/US2019/028135 on Apr. 18, 2019.

(60) Provisional application No. 62/793,491, filed on Jan. 17, 2019, provisional application No. 62/659,872, filed on Apr. 19, 2018.

(51) Int. Cl.
*A61K 31/18* (2006.01)

(52) U.S. Cl.
CPC .................................... *A61K 31/18* (2013.01)

(58) Field of Classification Search
CPC ...................................................... A61K 31/18
See application file for complete search history.

(56) References Cited

U.S. PATENT DOCUMENTS

| | | | |
|---|---|---|---|
| 4,279,909 | A | 7/1981 | Takashima |
| 6,492,428 | B1 | 12/2002 | Al-Abed et al. |
| 6,608,101 | B1 | 8/2003 | Ni et al. |
| 8,779,001 | B2 | 7/2014 | Tweardy et al. |
| 10,112,933 | B2 | 10/2018 | Tweardy et al. |
| 10,676,455 | B2 | 6/2020 | Tweardy et al. |
| 2004/0048795 | A1 | 3/2004 | Ivanova et al. |
| 2005/0239886 | A1 | 10/2005 | Hamuro et al. |
| 2005/0287664 | A1 | 12/2005 | Fann |
| 2006/0148715 | A1 | 7/2006 | Tweardy |
| 2007/0004704 | A1 | 1/2007 | Damon et al. |
| 2007/0203236 | A1 | 8/2007 | Smith et al. |
| 2009/0221542 | A1 | 9/2009 | Wang et al. |
| 2010/0035793 | A1 | 2/2010 | Lim et al. |
| 2010/0041685 | A1 | 2/2010 | Tweardy et al. |
| 2010/0209950 | A1 | 8/2010 | Gernez et al. |
| 2011/0312984 | A1 | 12/2011 | Tweardy et al. |
| 2012/0035163 | A1 | 2/2012 | Yasuma et al. |
| 2012/0040917 | A1 | 2/2012 | Orum et al. |
| 2012/0178718 | A1 | 7/2012 | Nique et al. |
| 2013/0123266 | A1 | 5/2013 | Zagury et al. |
| 2014/0088171 | A1 | 3/2014 | Yan et al. |
| 2014/0296270 | A1 | 10/2014 | Tweardy et al. |
| 2015/0031714 | A1 | 1/2015 | Tweardy et al. |
| 2015/0038443 | A1 | 2/2015 | Li et al. |
| 2020/0331880 | A1 | 10/2020 | Tweardy et al. |

FOREIGN PATENT DOCUMENTS

| | | |
|---|---|---|
| WO | 2007136858 A2 | 11/2007 |
| WO | 2009149192 A1 | 12/2009 |
| WO | 2012017166 A2 | 2/2012 |
| WO | 2013078372 A1 | 5/2013 |

OTHER PUBLICATIONS

Rosenbloom, Biochimica et Biophysica Acta 1832 (2013) 1088-1103 (Year: 2013).*
NIH (Fibrotic Diseases: causes, consequences, prevention, and treatment) (Year: 2020).*
Mandal, (https://www.news-medical.net/health/Types-of-Fibrosis.aspx) (Year: 2019).*
U.S. Appl. No. 12/477,583 Office Action dated Aug. 30, 2012.
Xu, X., et al., "Chemical Probes that Competitively and Selectively Inhibit Stat3 Activation", PLoS One, 4(3): e4783, (Mar. 2009).
U.S. Appl. No. 14/335,853 Office Action dated Feb. 1, 2016.
McMurray, J.S., "Structural Basis for the Binding of High Affinity Phosphopeptides to Stat3", PeptideScience, 90(1):69-79, (Nov. 27, 2007).
U.S. Appl. No. 14/335,853 Office Action dated Sep. 29, 2016.
U.S. Appl. No. 14/335,853 Office Action dated Mar. 13, 2017.
Hakala, M., "Poor prognosis in patients with rheumatoid arthritis hospitalized for interstitial lung fibrosis", Chest, 93:114-118, (1988).
Lindsay, K., et al., "Liver fibrosis in patients with psoriasis and psoriatic arthritis on long-term, high cumulative dose methotrexate therapy", Rheumatology, 48:569-572, (2009).
U.S. Appl. No. 14/335,804 dated May 17, 2016.
Fan, D., et al., "Cardic fibroblasts, fibrosis and extracellular matrix remodeling in heart disease", Fibrogenesis & Tissue Repair, 5:15 (2012).
U.S. Appl. No. 14/335,804 Office Action dated May 16, 2017.
Avery, D.T., et al., "STAT3 is required for IL-21-induced secretion of IgE from human naive B cells", Blood, 112(5): 1784-1793 (Sep. 1, 2008).
U.S. Appl. No. 14/335,829 Office Action dated Jun. 12, 2015.
U.S. Appl. No. 14/335,829 Office Action dated Nov. 7, 2018.
Kang, N., et al., "Tumor Necrosis Factor-alpha Develops Late Anaphylactic Reaction through Cytosolic Phospholipase A(2) Activation", Int. Arch. Allergy Immunol. 147(4): 315-322 (Aug. 2008).
U.S. Appl. No. 14/335,829 Office Action dated Oct. 25, 2019.

(Continued)

*Primary Examiner* — Umamaheswari Ramachandran
(74) *Attorney, Agent, or Firm* — Goodwin Procter LLP

(57) ABSTRACT

Compounds as STAT3 inhibitors are described. A pharmaceutical composition comprising the same, methods of making the same, and a method for treating or preventing conditions such as cancer, chronic inflammation, and fibrosis using the same, are described.

6 Claims, 1 Drawing Sheet

(56) References Cited

OTHER PUBLICATIONS

Choi, I., et al., "TNF-a induces the late-phase airway hyperresponsiveness and airway inflammation through cytosolic phospholipase A(2) activation", J. Allergy Clin. Immunol., 116:537-543, (Sep. 2005).
U.S. Appl. No. 14/335,829 Office Action dated Feb. 28, 2020.
Pubchem-CID: 247699, pp. 1-13, (Mar. 26, 2005).
Mak, R.H., et al., "Wasting in chronic kidney disease", J. Cachexia Sarcopenia Muscle, 2:9-25, (Mar. 2011).
Morley, J.E., et al., "Cachexia: pathophysiology and clinical relevance", Am J. Clin Nutr., 83(4): 735-743, (Apr. 2006).
Silva, et al., "A New therapeutical approach to block cancer cachexia: focusing inhibition of STAT3", The FASEB Journal, 27(S1):2 pgs, Abstract (2013).
Pedroza, M., et al., "Role of STAT3 in skin fibrosis and transforming growth factor beta signalling", Rheumatology, 57: 1838-1850 (2018).
Gavino, A.C., et al., "Small-Molecule Inhibition of STAT3 Prevents House-Dust-Mite (HDM)-Induced Airway Inflammation by Blocking Lung Production of Th17 and Th2 Cytokines", J Allergy Clin Immunol (Feb. 2014).
Debnath, B., et al., "Small Molecule Inhibitors of Signal Transducer and Activator of Transcription 3 (Stat3) Protein", J. Med. Chem., 55: 6645-6668, (2012).
U.S. Appl. No. 12/477,583 dated Nov. 9, 2011.
U.S. Appl. No. 12/477,583 dated May 23, 2013.
U.S. Appl. No. 14/335,853 Office Action dated Oct. 6, 2017.
U.S. Appl. No. 14/335,853 Office Action dated May 17, 2018.
U.S. Appl. No. 14/335,853 Office Action dated Feb. 5, 2019.
U.S. Appl. No. 14/335,853 Office Action dated Jul. 9, 2019.
U.S. Appl. No. 14/335,853 Office Action dated Nov. 29, 2019.
U.S. Appl. No. 14/335,804 Office Action dated Oct. 16, 2015.
U.S. Appl. No. 14/335,804 Office Action dated May 7, 2015.
U.S. Appl. No. 14/335,829 Office Action dated Sep. 22, 2020.
U.S. Appl. No. 14/335,829 Office Action dated Jun. 19, 2019.
U.S. Appl. No. 14/335,829 Office Action dated Apr. 13, 2018.
U.S. Appl. No. 14/335,829 Office Action dated May 10, 2017.
U.S. Appl. No. 14/335,829 Office Action dated Jan. 5, 2017.
U.S. Appl. No. 14/335,829 Office Action dated May 13, 2016.
U.S. Appl. No. 14/335,829 Office Action dated Nov. 4, 2015.
Bharadwaj, U., et al., STAT3 Inhibitors in Cancer: A comprehensive update, in A.C. Ward (ed.) STAT Inhibitors in Cancer, Cancer Drug Discovery and Development, Springer International Publishing: Switzerland, pp. 95-161 (2016).
Denton, C.P., et al., Therapeutic interleukin-6 blockade reverses transforming growth factor-beta pathway activation in dermal fibroblasts: insights from the faSScinate clinical trial in systemic sclerosis, Ann Rheum Dis, 0:1-10 (2018).
PCT/US2019/028135 International Search Report and Written Opinion dated Jul. 5, 2019.

\* cited by examiner

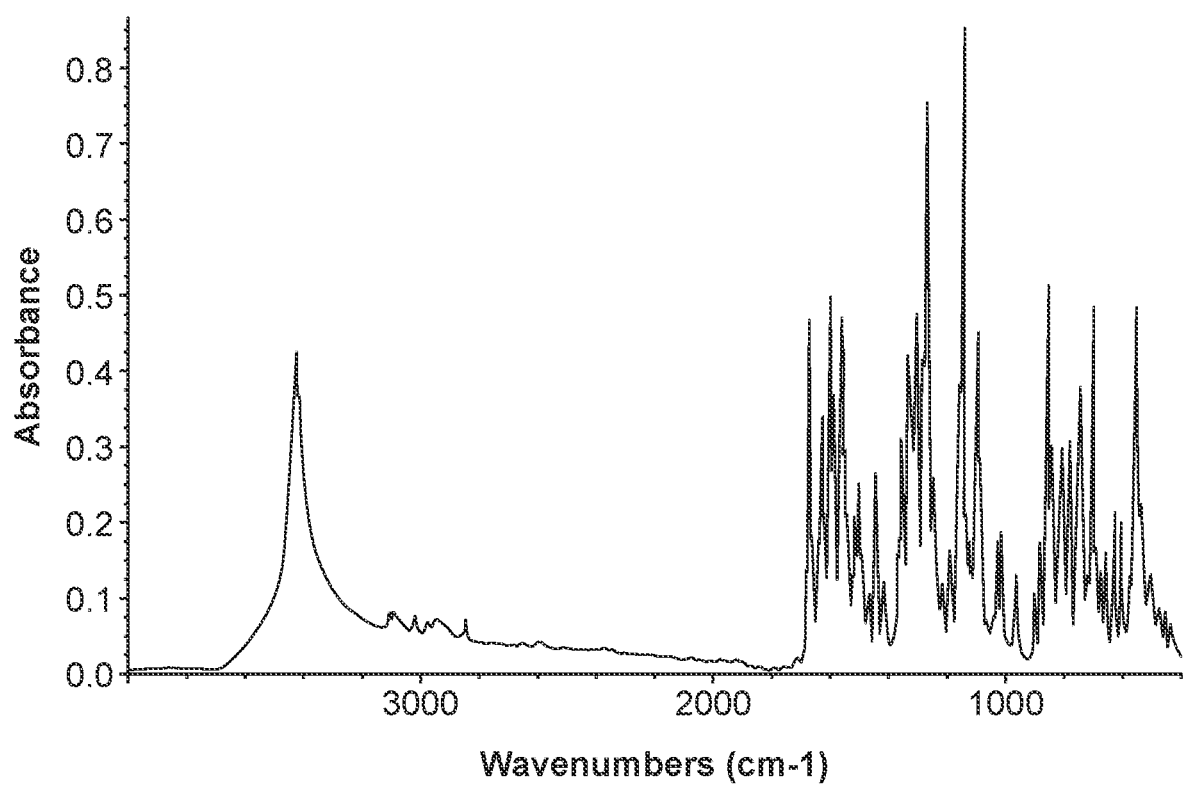

STAT3 INHIBITORS

CROSS-REFERENCES TO RELATED APPLICATIONS

This application is a continuation of U.S. application Ser. No. 17/048,602, filed on Oct. 18, 2020, which is the U.S. National Phase entry of International Application No. PCT/US2019/028135, filed on Apr. 18, 2019, which claims the benefit and priority to U.S. Provisional Application No. 62/659,872, filed on Apr. 19, 2018, and U.S. Provisional Application No. 62/793,491, filed on Jan. 17, 2019, the contents of each are hereby incorporated by reference in their entirety.

INCORPORATION BY REFERENCE

All patents, patent applications and publications cited herein are hereby incorporated by reference in their entirety in order to more fully describe the state of the art as known to those skilled therein as of the date of the invention described herein.

FIELD OF THE INVENTION

The invention relates generally to the field of pharmaceutical science. More particularly, the invention relates to compounds and compositions useful as pharmaceuticals for inhibiting STAT3. More specifically, the invention relates to compounds and their use in methods for treating conditions such as cancer, chronic inflammation, and fibrosis.

BRIEF DESCRIPTION OF THE DRAWINGS

FIG. 1 illustrates an IR spectrum of Compound of Formula III.

BACKGROUND

Signal transducer and activator of transcription 3 (STAT3) is one of seven members of the STAT protein family, which are signaling intermediates that mediate the actions of many cytokines and growth factors. In addition, STAT3 is an oncogene. See Bromberg, J. F., et al., *STAT3 as an oncogene*, CELL, 1998, 295-303; published erratum appears in CELL, 1999 Oct. 15, 1999(2), 239. STAT3 is constitutively active in many different cancers including prostate, breast, lung, squamous cell carcinoma of the head and neck, multiple myeloma, colon cancer, hepatocellular carcinomas, and large granular lymphocytic leukemia. Furthermore, human tumor xenograft studies in mice have repeatedly demonstrated that targeting STAT3 either genetically or pharmacologically results in decreased tumor growth and improved animal survival by inducing apoptosis in tumor cells, inhibiting angiogenesis, and enhancing anti-tumor immune-mediated cytotoxicity. See, e.g., Redell, M. S., et al., *Targeting transcription factors in cancer: Challenges and evolving strategies*, DRUG DISCOVERY TODAY, TECHNOLOGIES, 2006 3(3): 261-267; Kato, T., et al., *Proteolytic Conversion of STAT3 {alpha} to STAT3 {gamma} in Human Neutrophils: Role of Granule derived Serine Proteases*, J. BIOL. CHEM., 2004, 279(30): 31076-31080; Dunn, G. P., et al., *Cancer immunoediting: from immunosurveillance to tumor escape*, NAT. IMMUNOL., 2002, 3(11): 991-998. Thus, STAT3 has been identified as a potential target for drug development to treat cancers.

Muscle wasting is a debilitating complication of catabolic conditions including chronic kidney disease (CKD), diabetes, cancer, or serious infections. In mice with CKD, inhibition of myostatin reduced circulating levels of IL-6 and TNFα, suggesting a link between inflammation and muscle wasting as reported in clinical studies. See Carrero, J. J., et al., *Muscle atrophy, inflammation and clinical outcome in incident and prevalent dialysis patients*, CLIN. NUTR., 2008, 27, 557-564. STAT3 was found to be activated by the IL-6 family of cytokines, thus suggesting that the STAT3 pathway could be linked to loss of muscle mass. See Hirano, T., et al., *Signaling mechanisms through gp 130: a model of the cytokine system*, CYTOKINE GROWTH FACTOR REV., 1997, 8, 241-252.

Fibrosis is a pathological process involving the accumulation of excessive extra-cellular matrix in tissues, leading to tissue damage and organ dysfunction, which can progress to organ failure and death. In systemic sclerosis, an idiopathic fibrosis disease, the trigger is postulated to be an autoimmune response that leads to tissue injury, production of growth factors, pro-inflammatory and pro-fibrotic cytokines, and accumulation of myofibroblasts. Two potential sources of myofibroblasts are the differentiation of local fibroblasts and the process of epithelial-to-mesenchymal transition (EMT). IL-6 is a proinflammatory and profibrotic cytokine increasingly recognized as an important mediator of fibrosis that may contribute to the accumulation of myofibroblasts. After engaging its receptor, IL-6 signals through the STAT3. Thus, STAT3 represents a potentially important protein to target to treat fibrosis.

Asthma

Asthma affects 10% of the population worldwide and its prevalence has been increasing over the last decade. See Akinbami L J, Moorman J E, Bailey C, Zahran H S, King M, Johnson C A, et al., *Trends in asthma prevalence, health care use, and mortality in the United States, 2001-e2010*, NCHS DATA BRIEF, NO 94, HYATTSVILLE, Md.: NATIONAL CENTER FOR HEALTH STATISTICS, 2012. Asthma is a heterogeneous disease with multiple variants, the most widely recognized of which is the Th2-phenotype, characterized by atopy, eosinophilia, and responsiveness to steroids. See, e.g., Fahy J. V., *Eosinophilic and neutrophilic inflammation in asthma: insights from clinical studies*, PROC AM THORAC SOC 2009, 6(3) 256-9; Wenzel S. E., *Asthma: defining of the persistent adult phenotypes*, LANCET 2006, 368(9537): 804-13; Lin T, Poon A H, Hamid Q., *Asthma phenotypes and endotypes*, CURR OPIN PULM MED. 2013, 19(1):18-23. However, as many as 10% of patients have the Th17-phenotype of asthma which is non-atopic, neutrophilic, and steroid-resistant ("*Proceedings of the ATS workshop on refractory asthma: current understanding, recommendations, and unanswered questions*," AM J RESPIR CRIT CARE MED 2000; 162(6):2341-51; Al-Ramili W, Prefontaine D, Chouiali F, Martin J G, Olivenstein R, Lemiere C, et al., *T(H)17-associated cytokines (IL-17A and IL-17F) in severe asthma*, J ALLERGY CLIN IMMUNOL 2009; 123(5):1185-7; McKinley L, Alcorn J F, Peterson A, Dupont R B, Kapadia S, Logar A, et al., *Th17 cells mediate steroid-resistant airway inflammation and airway hyperresponsiveness in mice*, J IMMUNOL 2008; 181(6):4089-97); resulting in a higher morbidity and mortality owing to the lack of available effective treatments. Al-Ramili W, Prefontaine D, Chouiali F, Martin J G, Olivenstein R, Lemiere C, et al., *T(H)17-associated cytokines (IL-17A and IL-17F) in severe asthma*, J ALLERGY CLIN IMMUNOL 2009, 123(5):1185-7; Newcomb D C, Peebles R S Jr. *Th-17 mediated inflamma-* tion in asthma, CURR OPIN IMMUNOL 2013; 25(6):755-60. Alternative therapeutic options clearly are needed for this subset of patients.

Signal transducer and activator of transcription 3 (STAT3) is essential for Th17 lymphocyte development and cytokine production and its activation is linked to the development of airway inflammation. Harris T J, Grosso J F, Yen H, Xin H, Kortylewski M, Albesiano E, et al., *Cutting edge: an in vivo requirement for STAT3 signaling in Th17 development and Th17-dependent autoimmunity*, J IMMUNOL 2007, 179(7): 4333-7; Zhou L, Ivanov I I, Spolski R, Min R, Shenderov K, Egawa T, et al., *IL-6 programs T(H)-17 cell differentiation by promoting sequential engagement of the IL-21 and IL-23 pathways*, NAT IMMUNOL 2007, 8(9):967-74. Upon activation, STAT3 is recruited to cytokine-activated receptor complexes and becomes phosphorylated at Tyr (Y) 705. Phosphotyrosylated (p) STAT3 homodimerizes through reciprocal SH2-pY705 interactions, translocates to the nucleus, and binds to promoters to transcriptionally activate genes that drive Th17 differentiation and production of multiple cytokines. Sakaguchi M, Oka M, Iwasaki T, Fukami Y, Nishigori C., Role and regulation of STAT3 phosphorylation at Ser727 in melanocytes and melanoma cells, J INVEST DERMATOL 2012; 132(7):1877-85; Darnell J E Jr., *STATs and gene regulation*, SCIENCE 1997, 227(5332):1630-5. STAT3 activation also is involved in Th2 cytokine production (Doganci A, Eigenbrod T, Krug N, De Sanctis G T, Hausding M, Erpenbeck V J, et al., *The IL-6R alpha chain controls lung CD4+CD25+ Treg development and function during allergic airway inflammation in vivo*, J CLIN INVEST 2005, 115(2):313-25; Finotto S, Eigenbrod T, Karwot R, Boross I, Doganci A, Ito H, et al., *Local blockade of IL-6R signaling induces lung CD4+ T cell apoptosis in a murine model of asthma via regulatory T cells*, INT, IMMUNOL., 2007, 19(6):685-93; Simeone-Penney M C, Svergnini M, Tu P, Homer R J, Mariana T J, Cohn L, et al., *Airway epithelial STAT3 is required for allergic inflammation in a murine model of asthma*, J. IMMUNOL. 2007, 178(10):6191-9; Stritesky G L, Muthukrishnan R, Sehra S, Goswami R, Pham D, Travers J, et al., *The transcription factor STAT3 is required for T helper 2 cell development*, IMMUNITY 2011, 34(1):39-49), making it an attractive target for asthma treatment.

Anaphylaxis

Despite a significant burden of eczematous skin disease and elevations in both total and allergen-specific serum IgE, clinical food allergy and anaphylaxis are markedly diminished in patients with autosomal dominant hyper-IgE syndrome (AD-HIES) caused by STAT3 mutations. STAT3-silenced mast cells fail to degranulate normally due to a proximal FcεRI signaling defect. Siegel, A. M. et al. Diminished allergic disease in patients with STAT3 mutations reveals a role for STAT3 signaling in mast cell degranulation, THE JOURNAL OF ALLERGY AND CLINICAL IMMUNOLOGY, 132, 1388-1396, doi:10.1016/j.jaci.2013.08.045 (2013). Given that the STAT3-dependent cytokine IL-6 can lead to vascular leak (Wei, L. H. et al., *The role of IL-6 trans-signaling in vascular leakage: implications for ovarian hyperstimulation syndrome in a murine model*, THE JOURNAL OF CLINICAL ENDOCRINOLOGY AND METABOLISM, 98, E472-484, doi:10.1210/jc.2012-3462 (2013)) and STAT3 signaling is involved in gap junction dynamics (Guy, S., Geletu, M., Arulanandam, R. & Raptis, L., Stat3 and gap junctions in normal and lung cancer cells, CANCERS 6, 646-662, doi:10.3390/cancers6020646 (2014)), impaired STAT3 function may also protect against endothelial permeability during anaphylaxis. Histamine-induced anaphylaxis was blunted in STAT3 mutant AD-HIES mice and in wild-type mice subjected to small molecule STAT3 inhibition. Likewise, histamine skin prick responses were diminished in AD-HIES patients. Human umbilical vein vascular endothelial cells (HUVECs) derived from patients with AD-HIES or treated with a STAT3 inhibitor failed to properly signal through Src or to downregulate adherens junction proteins vascular endothelial (VE)-Cadherin and β-catenin. Diminished STAT3-target mir17-92 expression in AD-HIES HUVECS was associated with increases in PTEN—which inhibits Src, and E2F1—which regulates Q-catenin cellular dynamics. Thus, STAT3-dependent transcriptional activity regulates critical components for the architecture and functional dynamics of endothelial junctions and permeability. Long-term functional ablation of STAT3 prevents vascular mediator-induced dissolution of adherens junctions, and suggests that clinical conditions of excess vascular permeability, such as anaphylaxis, can be modulated via small molecule inhibition of STAT3.

Following mast cell degranulation, mediators such as histamine, platelet activating factor (PAF), and thrombin act on target vascular endothelium to increase nitric oxide synthesis (Palmer, R. M., Ferrige, A. G. & Moncada, S., *Nitric oxide release accounts for the biological activity of endothelium-derived relaxing factor*, NATURE 327, 524-526, doi:10.1038/327524a0 (1987)), intracellular calcium release (Valone, F. H. & Johnson, B., *Modulation of platelet-activating-factor-induced calcium influx and intracellular calcium release in platelets by phorbol esters*, THE BIOCHEMICAL JOURNAL, 247, 669-674 (1987); Kotlikoff, M. I., Murray, R. K. & Reynolds, E. E., *Histamine-induced calcium release and phorbol antagonism in cultured airway smooth muscle cells*, THE AMERICAN JOURNAL OF PHYSIOLOGY 253, C561-566 (1987)), and vascular leak, resulting in symptoms of immediate hypersensitivity (Kaliner, M., Sigler, R., Summers, R. & Shelhamer, J. H., *Effects of infused histamine: analysis of the effects of H-1 and H-2 histamine receptor antagonists on cardiovascular and pulmonary responses*, THE JOURNAL OF ALLERGY AND CLINICAL IMMUNOLOGY, 68, 365-371 (1981); Kirsch, C. M., Brokaw, J. J., Prow, D. M. & White, G. W., *Mechanism of platelet activating factor-induced vascular leakage in the rat trachea*, EXPERIMENTAL LUNG RESEARCH, 18, 447-459 (1992)). Endothelial adherens junctions regulate vascular leak and are formed by VE-cadherin linked by its cytoplasmic tail to intracellular anchors such as alpha-catenin, β-catenin, and plakoglobin (Andriopoulou, P., Navarro, P., Zanetti, A., Lampugnani, M. G. & Dejana, E., *Histamine induces tyrosine phosphorylation of endothelial cell-to-cell adherens junctions*, ARTERIOSCLEROSIS, THROMBOSIS, AND VASCULAR BIOLOGY, 19, 2286-2297 (1999)). Vascular permeability can be achieved by uncoupling VE-cadherin from β-catenin via a Src/Yes kinase-dependent mechanism (Wallez, Y. et al., *Src kinase phosphorylates vascular endothelial-cadherin in response to vascular endothelial growth factor: identification of tyrosine 685 as the unique target site*, ONCOGENE 26, 1067-1077, doi:10.1038/sj.onc.1209855 (2007); Weis, S., Cui, J., Barnes, L. & Cheresh, D., *Endothelial barrier disruption by VEGF-mediated Src activity potentiates tumor cell extravasation and metastasis*, THE JOURNAL OF CELL BIOLOGY 167, 223-229, doi: 10.1083/jcb.200408130 (2004)).

STAT3 signaling has been implicated in gap junction intercellular communication, IL-6- and IL11-induced vascular leakage, down-regulation of VE-cadherin concomitant with phosphorylation of STAT3, and the STAT3/mir17-92/E2F1 dependent regulation of β-catenin nuclear translocation and transcriptional activity. See, e.g., Wei, L. H. et al., *The role of IL-6 trans-signaling in vascular leakage: impli-* cations for ovarian hyperstimulation syndrome in a murine model, THE JOURNAL OF CLINICAL ENDOCRINOLOGY AND METABOLISM 98, E472-484, doi:10.1210/jc.2012-3462 (2013); Guy, S., Geletu, M., Arulanandam, R. & Raptis, L., *Stat3 and gap junctions in normal and lung cancer cells*, CANCERS 6, 646-662, doi:10.3390/cancers6020646 (2014); Snyder-Talkington, B. N., Schwegler-Berry, D., Castranova, V., Qian, Y. & Guo, N. L., *Multi-walled carbon nanotubes induce human microvascular endothelial cellular effects in an alveolar-capillary co-culture with small airway epithelial cells*, PARTICLE AND FIBRE TOXICOLOGY 10, 35, doi:10.1186/1743-8977-10-35 (2013); Dai, B. et al., *STAT3 mediates resistance to MEK inhibitor through microRNA miR-17*, CANCER RESEARCH 71, 3658-3668, doi:10.1158/0008-5472. CAN-10-3647 (2011); van Haaften, G. & Agami, R., *Tumorigenicity of the miR-17-92 cluster distilled*, GENES & DEVELOPMENT 24, 1-4, doi:10.1101/gad.1887110 (2010); Kawada, M. et al., *Signal transducers and activators of transcription 3 activation is involved in nuclear accumulation of beta-catenin in colorectal cancer*, CANCER RESEARCH 66, 2913-2917, doi:10.1158/0008-5472. CAN-05-3460 (2006); Mahboubi, K., Biedermann, B. C., Carroll, J. M. & Pober, J. S., *IL-11 activates human endothelial cells to resist immune-mediated injury*, JOURNAL OF IMMUNOLOGY 164, 3837-3846 (2000). Thus, STAT3 inhibition would be anticipated to reduce vascular permeability in the setting of anaphylaxis.

Inflammatory Bowel Disease (IBD)

IBD presents as either ulcerative colitis (UC) or Crohn's disease (CD). The etiology of UC and CD are not established, although several genes have been implicated as risk factors for IBD in genome-wide association studies (GWAS), including ATG16L, NOD2/CARD15, IBD5, CTLA4, TNFSF15, JAK2, STAT3, IL23R, and ORMDL3, which implicate antimicrobial peptides, innate and adaptive immune cell function, Th17 cells, regulatory T cells (Tregs), and cytokines (tumor necrosis factor, interleukins 17, 23, 12, 22, and IL-6). Many of these cytokines serve as ligands for cell surface receptors that activate STAT3. STAT3 within three cell lineages—myeloid cells, enterocytes, and T cells—has been demonstrated to contribute to colitis in mice and humans (Takeda K, Clausen B E, Kaisho T, et al., *Enhanced Th1 activity and development of chronic enterocolitis in mice devoid of Stat3 in macrophages and neutrophils*, IMMUNITY 1999, 10:39-49; Atreya R, Mudter J, Finotto S, et al., *Blockade of interleukin 6 trans signaling suppresses T-cell resistance against apoptosis in chronic intestinal inflammation: evidence in crohn disease and experimental colitis in vivo*, NAT MED 2000, 6:583-8; Suzuki A, Hanada T, Mitsuyama K, et al., *CIS3/SOCS3/SSI3 plays a negative regulatory role in STAT3 activation and intestinal inflammation*, J. EXP. MED. 2001, 193:471-81), but with contrasting effects. On the one hand, genetic deletion of STAT3 within myeloid cells (neutrophils and macrophages) or enterocytes resulted in chronic murine colitis or rendered mice more susceptible to experimental colitis, respectively. Pickert G, Neufert C, Leppkes M, et al., *STAT3 links IL-22 signaling in intestinal epithelial cells to mucosal wound healing*, THE JOURNAL OF EXPERIMENTAL MEDICINE, 2009, 206:1465-72. Thus, STAT3 within myeloid cells and enterocytes appears to protect against colitis. On the other hand, more recent studies in mice demonstrated that STAT3 within infiltrating CD4+ T cells prevents their apoptosis, which contributes to chronic intestinal inflammation (reviewed in Atreya R, Neurath M F, *Signaling molecules: the pathogenic role of the IL-6/STAT-3 trans signaling pathway in intestinal inflammation and in colonic cancer*, CURR DRUG TARGETS 2008, 9:369-74) indicating that STAT3 activation within T cells is necessary for chronic colitis.

Results from our studies examining the effects of modulating STAT3 activity either genetically or pharmacologically in two mouse models of IBD-dextran sodium salt (DSS; UC model) and trinitrobenzoic acid (TNBS; CD model) indicate the net effect of STAT3 across all cells and tissues is to promote the development of IBD. In addition to our findings in mice, other groups have shown that levels of activated STAT3 (pY-STAT3) were directly correlated with extent of inflammation in intestinal tissues from humans with IBD. Musso A, Dentelli P, Carlino A, et al., *Signal transducers and activators of transcription 3 signaling pathway: an essential mediator of inflammatory bowel disease and other forms of intestinal inflammation*, INFLAMM BOWEL DIS., 2005, 11:91-8; Mudter J, Weigmann B, Bartsch B, et al., *Activation pattern of signal transducers and activators of transcription (STAT) factors in inflammatory bowel diseases*, AM J GASTROENTEROL, 2005, 100:64-72; Mitsuyama K, Matsumoto S, Masuda J, et al., *Therapeutic strategies for targeting the IL-6/STAT3 cytokine signaling pathway in inflammatory bowel disease*, ANTICANCER RESEARCH 2007, 27:3749-56. Thus, targeting STAT3 may represent an effective means of treating IBD patients refractory to current standards of care.

Therefore, there remains a need to develop novel compounds and methods for modulating or inhibiting STAT3 activities.

SUMMARY OF THE INVENTION

In one aspect, compounds or pharmaceutically acceptable salts thereof useful as STAT3 modulators or inhibitors having the structure of Formula I are described herein,

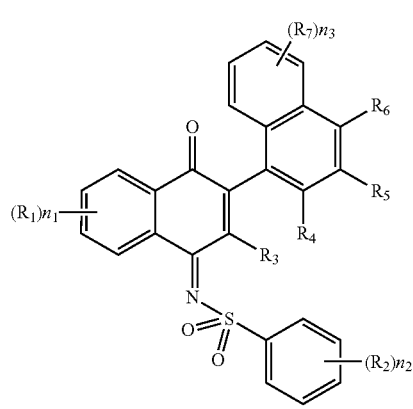

where the various substituents are defined in one or more embodiments herein. The compounds described herein modulate (e.g., inhibit) STAT3 and thus can be useful as treatment of one or more of the disorders described herein. Methods for synthesizing these compounds are also described herein. Compositions and methods described herein are useful for inhibiting STAT3 in vitro and in vivo. Such compositions and methods thus are useful in a number of clinical applications, including as pharmaceutical agents and methods for treating disorders or conditions involving unwanted STAT3 activities. Non-limiting examples of the disorders include anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, astrogliosis due to Alzheimer's or other neurodegenerative disease, and a combination thereof.

In one aspect, a compound of Formula I,

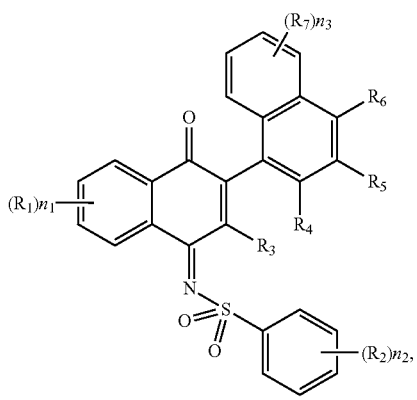

I or a pharmaceutically acceptable salt thereof is described, where each occurrence of $R_1$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_1$ is 0, 1, 2, 3, or 4;

each occurrence of $R_2$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, cycloalkenyl, optionally substituted aryl, optionally substituted aryloxyl, or optionally substituted heterocycle;

$n_2$ is 0, 1, 2, 3, 4, or 5;

$R_3$ is hydrogen, halogen, cyano, nitro, $CF_3$, $OCF_3$, $OR_a$, $SR_a$, $OC(=O)R_a$, alkyl, alkenyl, cycloalkyl, or optionally substituted aryl or heteroaryl;

$R_4$ is hydrogen, halogen, cyano, nitro, $CF_3$, $OCF_3$, $OR_a$, $SR_a$, $NR_bR_c$, $OC(=O)R_a$, alkyl, alkenyl, or cycloalkyl;

each occurrence of $R_5$, $R_6$, and $R_7$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_3$ is 0, 1, 2, 3, or 4; and each occurrence of $R_a$, $R_b$, and $R_c$ is independently hydrogen, alkyl, cycloalkyl, alkenyl, cycloalkenyl, alkynyl, heterocycle, or aryl; or said $R_b$ and $R_c$ together with the nitrogen atom to which they are bonded optionally form a heterocycle comprising 1-4 heteroatoms.

In any one or more of the embodiments described herein, each occurrence of $R_1$ is independently hydrogen, halogen, cyano, nitro, $CF_3$, $OCF_3$, $OR_a$, or $SR_a$.

In any one or more of the embodiments described herein, each occurrence of $R_1$ is independently $C(=O)R_a$, $OC(=O)R_a$, $C(=O)OR$, $NR_aR_b$, $NR_bC(=O)R_a$, $C(=O)NR_bR_c$, $NR_bC(=O)OR_a$, $OC(=O)NR_bR_c$, or $NR_aC(=O)NR_bR_c$.

In any one or more of the embodiments described herein, each occurrence of $R_1$ is independently alkyl, alkenyl, cycloalkyl, optionally substituted aryl, or optionally substituted heterocycle.

In any one or more of the embodiments described herein, $R_1$ is H.

In any one or more of the embodiments described herein, $n_1$ is 0, 1, or 2.

In any one or more of the embodiments described herein, $n_1$ is 1.

In any one or more of the embodiments described herein, $n_1$ is 0.

In any one or more of the embodiments described herein, each occurrence of $R_2$ is independently hydrogen, halogen, cyano, nitro, $CF_3$, $OCF_3$, $OR_a$, or $SR_a$.

In any one or more of the embodiments described herein, each occurrence of $R_2$ is independently $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_c$, or $NR_aC(=O)NR_bR_c$.

In any one or more of the embodiments described herein, each occurrence of $R_2$ is independently alkyl, alkenyl, cycloalkyl, optionally substituted aryl, or optionally substituted heterocycle.

In any one or more of the embodiments described herein, $R_2$ is H.

In any one or more of the embodiments described herein, $n_2$ is 0, 1, or 2.

In any one or more of the embodiments described herein, $n_2$ is 1.

In any one or more of the embodiments described herein, $n_2$ is 0.

In any one or more of the embodiments described herein, $R_3$ is hydrogen, halogen, cyano, nitro, or $CF_3$.

In any one or more of the embodiments described herein, $R_3$ is $OCF_3$, $OR_a$, $SR_a$, or $OC(=O)R_a$.

In any one or more of the embodiments described herein, $R_3$ is alkyl, alkenyl, or cycloalkyl.

In any one or more of the embodiments described herein, $R_3$ is H.

In any one or more of the embodiments described herein, $R_4$ is hydrogen, halogen, cyano, nitro, or $OR_a$.

In any one or more of the embodiments described herein, $R_4$ is $OCF_3$, $SR_a$, or $OC(=O)R_a$.

In any one or more of the embodiments described herein, $R_4$ is alkyl, alkenyl, or cycloalkyl.

In any one or more of the embodiments described herein, $R_4$ is OH.

In any one or more of the embodiments described herein, $R_4$ is OMe.

In any one or more of the embodiments described herein, $R_5$, $R_6$, and $R_7$ are each independently selected from the group consisting of hydrogen, halogen, cyano, nitro, and $CF_3$.

In any one or more of the embodiments described herein, $R_5$, $R_6$, and $R_7$ are each independently selected from the group consisting of $OCF_3$, $OR_a$, and $SR_a$.

In any one or more of the embodiments described herein, $R_5$, $R_6$, and $R_7$ are each independently selected from the group consisting of $OCF_3$ and $OR_a$.

In any one or more of the embodiments described herein, $R_5$, $R_6$, and $R_7$ are each independently selected from the group consisting of $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_c$, and $NR_aC(=O)NR_bR_c$.

In any one or more of the embodiments described herein, $R_5$, $R_6$, and $R_7$ are each independently selected from the group consisting of alkyl, alkenyl, cycloalkyl, optionally substituted aryl, and optionally substituted heterocycle.

In any one or more of the embodiments described herein, each occurrence of $R_5$, $R_6$, and $R_7$ is H.

In any one or more of the embodiments described herein, $n_3$ is 0, 1, or 2.

In any one or more of the embodiments described herein, $n_3$ is 1.

In any one or more of the embodiments described herein, $n_3$ is 0.

In any one or more of the embodiments described herein, each occurrence of $R_a$ is independently hydrogen, alkyl, heterocycle, or aryl.

In any one or more of the embodiments described herein, each occurrence of $R_a$ is independently hydrogen or alkyl.

In any one or more of the embodiments described herein, each occurrence of $R_b$ and $R_c$ is independently hydrogen, alkyl, heterocycle, or aryl.

In any one or more of the embodiments described herein, each occurrence of $R_b$ and $R_c$ is independently hydrogen or alkyl.

In any one or more of the embodiments described herein, $R_b$ and $R_c$ together with the nitrogen atom to which they are bonded optionally form a heterocycle comprising 1-4 heteroatoms each selected from the group consisting of N, O, and S.

In any one or more of the embodiments described herein, the compound of claim 1 has the structure of Formula II:

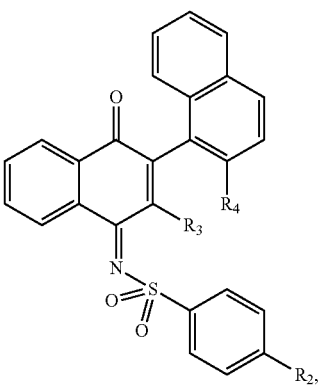

or a pharmaceutically acceptable salt thereof.

In any one or more of the embodiments described herein, $R_2$ is H, OH, alkyl, alkoxy, halogen, $NR_bR_c$, $CF_3$, $OCF_3$, or CN.

In any one or more of the embodiments described herein, $R_2$ is $NH_2$, OH, OMe, OEt, $OCH_2CH_2CH_3$, or $OCH(CH_3)_2$.

In any one or more of the embodiments described herein, $R_2$ is selected from the group consisting of hydrogen, methyl, ethyl, propyl, tert-butyl, F, Cl, Br, $CF_3$, nitro, methoxy, ethoxy, $OCF_3$, —C(=O)Me, —C(=O)OMe, —NHC(=O)Me, 1,4-dioxanyl, cyclohexanyl, cyclohexenyl, phenoxy, 2-methoxyphenoxy, 3-methoxyphenoxy, 4-methoxyphenoxy, 2-chlorophenoxy, 3-chlorophenoxy, 4-chlorophenoxy, 2-methylphenoxy, 3-methylphenoxy, and 4-methylphenoxy.

In any one or more of the embodiments described herein, $R_2$ is OMe.

In any one or more of the embodiments described herein, $R_3$ is H, OH, alkyl, alkoxy, or halogen.

In any one or more of the embodiments described herein, $R_3$ is H.

In any one or more of the embodiments described herein, $R_4$ is H, alkyl, OH, $NH_2$, alkoxy, halogen, $CF_3$, or CN.

In any one or more of the embodiments described herein, $R_4$ is H, OH, or alkoxy.

In any one or more of the embodiments described herein, $R_4$ is OH.

In any one or more of the embodiments described herein, $R_4$ is OMe.

In any one or more of the embodiments described herein, the compound has the structure of Formula III,

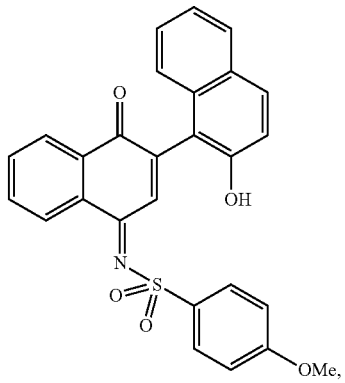

or a pharmaceutically-acceptable salt thereof.

In any one or more of the embodiments described herein, the compound is selected from the group consisting of the compounds in Table 1a, or a pharmaceutically acceptable salt thereof.

In any one or more of the embodiments described herein, the compound is selected from the group consisting of the compounds in Table 1b, or a pharmaceutically-acceptable salt thereof.

In another aspect, a pharmaceutical composition is described, including at least one compound according to any one of the embodiments disclosed herein, or a pharmaceutically acceptable salt thereof, and a pharmaceutically acceptable carrier or diluent.

In yet another aspect, a method of inhibiting STAT3 in a cell is described, including delivering to the cell an effective amount of at least one compound according to any one of the embodiments disclosed herein or a pharmaceutically acceptable salt thereof.

In any one or more of the embodiments described herein, the cell is in vivo in a mammal.

In any one or more of the embodiments described herein, the mammal is a human, a dog, a cat, a horse, a cow, a pig, a sheep, or a goat.

In any one or more of the embodiments described herein, the cell is a cancer cell.

In any one or more of the embodiments described herein, the method further includes inducing apoptosis in the cancer cell.

In any one or more of the embodiments described herein, the method further includes inhibiting angiogenesis in a tumor, enhancing anti-tumor immune-mediated cytotoxicity, decreasing tumor growth, improving the mammal's survival, inhibiting STAT3 phosphorylation, and/or inhibiting nuclear-to-cytoplasmic translocation of STAT3.

In any one or more of the embodiments described herein, the human is suffering from, or known, suspected, or at risk for developing a neurodegenerative disease, anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, astrogliosis in Alzheimer's or other neurodegenerative disease, or a combination thereof.

In any one or more of the embodiments described herein, the hyperproliferative disease is selected from the group consisting of head and neck cancer, lung cancer, liver cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, and leukemia.

In any one or more of the embodiments described herein, the leukemia is acute myelogenous leukemia.

In any one or more of the embodiments described herein, the fibrosis is selected from the group consisting of pulmonary fibrosis, bone marrow fibrosis, intestine fibrosis, pancreas fibrosis, joint fibrosis, liver fibrosis, retroperionteum, myelofibrosis, and dermal fibrosis.

In any one or more of the embodiments described herein, the viral infection is a chronic viral infection.

In any one or more of the embodiments described herein, the chronic viral infection is AIDS, HIV infection, Hepatitis B virus infection, Hepatitis C virus infection, or Epstein-Barr virus infection.

In any one or more of the embodiments described herein, the disorder is asthma, psoriasis, inflammatory bowel disease, uveitis, scleritis, multiple sclerosis, graft-versus-host diseases, pancreatitis, pulmonary lymphangioleiomyomatosis, age-related macular degeneration or amyloidosis.

In any one or more of the embodiments described herein, the anaphylaxis comprises anaphylactic shock.

In any one or more of the embodiments described herein, the disorder is selected from the group consisting of muscle wasting, muscle weakness, cachexia, and a combination thereof; and the human has or is at risk of having muscle wasting, cachexia, renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, visceral leishmaniasis, prolonged bed rest, or drug addiction.

In any one or more of the embodiments described herein, the chronic obstructive lung disease is emphysema.

In any one or more of the embodiments described herein, the neurodegenerative disease is chemotherapy-induced peripheral neuropathy, diabetic neuropathy or chemobrain.

In yet another aspect, a method of treating or preventing a disorder in a mammalian species in need thereof is described, including administering to the mammalian species a therapeutically effective amount of at least one compound according to any one of the embodiments disclosed herein or a pharmaceutically acceptable salt thereof, wherein the disorder is selected from the group consisting of a neurodegenerative disease, anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, astrogliosis in Alzheimer's or other neurodegenerative disease, and a combination thereof.

In any one or more of the embodiments described herein, the mammalian species is a human, a dog, a cat, a horse, a cow, a pig, a sheep, or a goat.

In any one or more of the embodiments described herein, the mammalian species is a human.

In any one or more of the embodiments described herein, the human is suffering from, at risk of having, or susceptible to have the disorder.

In any one or more of the embodiments described herein, the hyperproliferative disease is selected from the group consisting of head and neck cancer, lung cancer, liver cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, and leukemia.

In any one or more of the embodiments described herein, the leukemia is acute myelogenous leukemia.

In any one or more of the embodiments described herein, the fibrosis is selected from the group consisting of pulmonary fibrosis, bone marrow fibrosis, intestinal fibrosis, pancreatic fibrosis, joint fibrosis, liver fibrosis, retroperionteum, myelofibrosis, and dermal fibrosis.

In any one or more of the embodiments described herein, the viral infection is a chronic viral infection.

In any one or more of the embodiments described herein, the chronic viral infection is AIDS, HIV infection, Hepatitis B virus infection, Hepatitis C virus infection, or Epstein-Barr virus infection.

In any one or more of the embodiments described herein, the disorder is asthma, psoriasis, inflammatory bowel disease, uveitis, scleritis, multiple sclerosis, graft-versus-host diseases, pancreatitis, pulmonary lymphangioleiomyomatosis, age-related macular degeneration, or amyloidosis.

In any one or more of the embodiments described herein, the anaphylaxis comprises anaphylactic shock.

In any one or more of the embodiments described herein, the disorder is selected from the group consisting of muscle wasting, muscle weakness, cachexia, and a combination thereof; and the human has or is at risk of having muscle wasting, cachexia, renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long-bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis *nodosa*, sarcoidosis, systemic lupus erythematosus, visceral leishmaniasis, prolonged bed rest, or drug addiction.

In any one or more of the embodiments described herein, the chronic obstructive lung disease is emphysema.

In any one or more of the embodiments described herein, the neurodegenerative disease is chemotherapy-induced peripheral neuropathy, diabetic neuropathy, or chemobrain.

In yet another aspect, a method of making a compound of Formula I is described, including the step of oxidizing a compound of Formula Ix to form the compound of Formula I using an oxidation reagent in step a):

a)

Ix

→

I wherein each occurrence of $R_1$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_1$ is 0, 1, 2, 3, or 4;

each occurrence of $R_2$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, cycloalkenyl, optionally substituted aryl, optionally substituted aryloxyl, or optionally substituted heterocycle;

$n_2$ is 0, 1, 2, 3, 4, or 5;

$R_3$ is hydrogen, halogen, cyano, nitro, $CF_3$, $OCF_3$, $OR_a$, $SR_a$, $OC(=O)R_a$, alkyl, alkenyl, cycloalkyl, or optionally substituted aryl or heteroaryl;

$R_4$ is hydrogen, halogen, cyano, nitro, $CF_3$, $OCF_3$, $OR_a$, $SR_a$, $NR_bR_c$, $OC(=O)R_a$, alkyl, alkenyl, or cycloalkyl;

each occurrence of $R_5$, $R_6$, and $R_7$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_3$ is 0, 1, 2, 3, or 4; and each occurrence of $R_a$, $R_b$, and $R_c$ is independently hydrogen, alkyl, cycloalkyl, alkenyl, cycloalkenyl, alkynyl, heterocycle, or aryl; or said $R_b$ and $R_c$ together with the nitrogen atom to which they are bonded optionally form a heterocycle comprising 1-4 heteroatoms.

In any one or more of the embodiments described herein, the oxidation reagent is selected from the group consisting of $NaIO_4$, $H_2O_2$, MCPBA, and a combination thereof.

In any one or more of the embodiments described herein, the oxidation reagent is $NaIO_4$.

In any one or more of the embodiments described herein, $NaIO_4$ is prepared in situ.

In any one or more of the embodiments described herein, the oxidation reagent is used in the amount of 1.5-4.0 equivalence to the compound of Formula Ix.

In any one or more of the embodiments described herein, the oxidation reagent is used in the amount of 2.0-3.5 equivalence to the compound of Formula Ix.

In any one or more of the embodiments described herein, step a) is conducted for 12 hours to 2 days.

In any one or more of the embodiments described herein, step a) is conducted for 1 day.

In any one or more of the embodiments described herein, each occurrence of $R_1$ is independently hydrogen, halogen, cyano, nitro, $CF_3$, $OCF_3$, $OR_a$, or $SR_a$.

In any one or more of the embodiments described herein, each occurrence of $R_1$ is H.

In any one or more of the embodiments described herein, each occurrence of $R_2$ is independently halogen, cyano, nitro, $CF_3$, $OCF_3$, $OR_a$, or $SR_a$.

In any one or more of the embodiments described herein, $R_2$ is OMe and $n_2$ is 1.

In any one or more of the embodiments described herein, $R_3$ is $OCF_3$, $OR_a$, $SR_a$, $OC(=O)R_a$, alkyl, alkenyl, or cycloalkyl.

In any one or more of the embodiments described herein, $R_3$ is H.

In any one or more of the embodiments described herein, the compound of Formula I has the structure of Formula III,

III

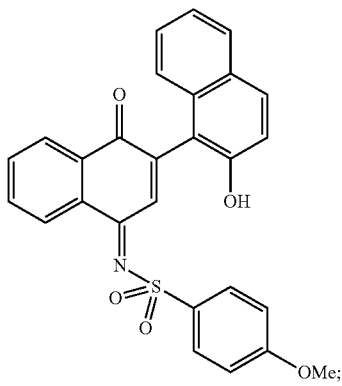

and the compound of Formula Ix has the structure of Formula IIIx,

IIIx

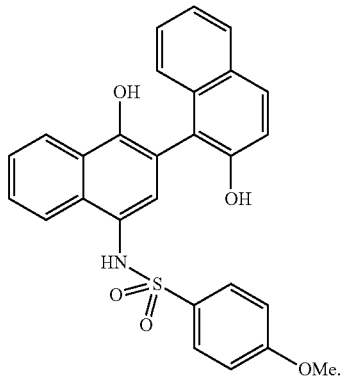

Any aspect or embodiment disclosed herein may be combined with another aspect or embodiment disclosed herein. The combination of one or more embodiments described herein with other one or more embodiments described herein is expressly contemplated.

FURTHER DESCRIPTION OF THE INVENTION

Definitions

The following are definitions of terms used in the present specification. The initial definition provided for a group or term herein applies to that group or term throughout the present specification individually or as part of another group, unless otherwise indicated. Unless otherwise defined, all technical and scientific terms used herein have the same meaning as commonly understood by one of ordinary skill in the art.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, n-butyl, t-butyl, isobutyl pentyl, hexyl, isohexyl, heptyl, 4,4-dimethylpentyl, octyl, 2,2,4-trimethylpentyl, nonyl, decyl, undecyl, dodecyl, and the like. The term "($C_1$-$C_4$) alkyl" refers to a straight or branched chain alkane (hydrocarbon) radical containing from 1 to 4 carbon atoms, such as methyl, ethyl, propyl, isopropyl, n-butyl, t-butyl, and isobutyl. "Substituted alkyl" refers to an alkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_a$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$, and Rd is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. In the aforementioned exemplary substituents, groups such as alkyl, cycloalkyl, alkenyl, alkynyl, cycloalkenyl, heterocycle, and aryl can themselves be optionally substituted.

The term "alkenyl" refers to a straight or branched chain hydrocarbon radical containing from 2 to 12 carbon atoms and at least one carbon-carbon double bond. Exemplary such groups include ethenyl or allyl. The term "$C_2$-$C_6$ alkenyl" refers to a straight or branched chain hydrocarbon radical containing from 2 to 6 carbon atoms and at least one carbon-carbon double bond, such as ethylenyl, propenyl, 2-propenyl, (E)-but-2-enyl, (Z)-but-2-enyl, 2-methy(E)-but-2-enyl, 2-methy(Z)-but-2-enyl, 2,3-dimethyl-but-2-enyl, (Z)-pent-2-enyl, (E)-pent-1-enyl, (Z)-hex-1-enyl, (E)-pent-2-enyl, (Z)-hex-2-enyl, (E)-hex-2-enyl, (Z)-hex-1-enyl, (E)-hex-1-enyl, (Z)-hex-3-enyl, (E)-hex-3-enyl, and (E)-hex-1,3-dienyl. "Substituted alkenyl" refers to an alkenyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_c$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_e$, $C(=O)OR_a$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$, and Rd is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "alkynyl" refers to a straight or branched chain hydrocarbon radical containing from 2 to 12 carbon atoms and at least one carbon to carbon triple bond. Exemplary such groups include ethynyl. The term "$C_2$-$C_6$ alkynyl" refers to a straight or branched chain hydrocarbon radical containing from 2 to 6 carbon atoms and at least one carbon-carbon triple bond, such as ethynyl, prop-1-ynyl, prop-2-ynyl, but-1-ynyl, but-2-ynyl, pent-1-ynyl, pent-2-ynyl, hex-1-ynyl, hex-2-ynyl, or hex-3-ynyl. "Substituted alkynyl" refers to an alkynyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$ and Rd is independently hydrogen, alkyl, cycloalkyl, heterocycle, aryl, or said $R_b$ and $R_c$, together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted.

The term "cycloalkyl" refers to a fully-saturated cyclic hydrocarbon group containing from 1 to 4 rings and 3 to 8 carbons per ring. "$C_3$-$C_7$ cycloalkyl" refers to cyclopropyl, cyclobutyl, cyclopentyl, cyclohexyl, or cycloheptyl. "Substituted cycloalkyl" refers to a cycloalkyl group substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$, and Rd is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "cycloalkenyl" refers to a partially unsaturated cyclic hydrocarbon group containing 1 to 4 rings and 3 to 8 carbons per ring. Exemplary such groups include cyclobutenyl, cyclopentenyl, cyclohexenyl, etc. "Substituted cycloalkenyl" refers to a cycloalkenyl group substituted with one more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_e$, and Rd is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "aryl" refers to cyclic, aromatic hydrocarbon groups that have 1 to 5 aromatic rings, especially monocyclic or bicyclic groups such as phenyl, biphenyl, or naphthyl. Where containing two or more aromatic rings (bicyclic, etc.), the aromatic rings of the aryl group may be joined at a single point (e.g., biphenyl), or fused (e.g., naphthyl, phenanthrenyl, and the like). "Substituted aryl" refers to an aryl group substituted by one or more substituents, preferably 1 to 3 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_dS(=O)_2NR_bR_c$, $NR_dP(=O)_2NR_bR_c$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_e$, and Rd is independently hydrogen, alkyl, cycloalkyl, heterocycle, aryl, or said $R_b$ and $R_c$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include fused cyclic groups, especially fused cycloalkyl, fused cycloalkenyl, fused heterocycle, or fused aryl, where the aforementioned cycloalkyl, cycloalkenyl, heterocycle, and aryl substituents can themselves be optionally substituted.

The term "carbocycle" refers to a fully saturated or partially saturated cyclic hydrocarbon group containing from 1 to 4 rings and 3 to 8 carbons per ring, or cyclic, aromatic hydrocarbon groups that have 1 to 5 aromatic rings, especially monocyclic or bicyclic groups such as phenyl, biphenyl, or naphthyl. The term "carbocycle" encompasses cycloalkyl, cycloalkenyl, cycloalkynyl, and aryl as defined hereinabove. The term "substituted carbocycle" refers to carbocycle or carbocyclic groups substituted with one or more substituents, preferably 1 to 4 substituents, at any available point of attachment. Exemplary substituents include, but are not limited to, those described above for substituted cycloalkyl, substituted cycloalkenyl, substituted cycloalkynyl, and substituted aryl. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The terms "heterocycle" and "heterocyclic" refer to fully saturated, or partially or fully unsaturated, including aromatic (i.e., "heteroaryl") cyclic groups (for example, 4 to 7 membered monocyclic, 7 to 11 membered bicyclic, or 8 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms, and/or sulfur atoms, where the nitrogen and sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heterocyclic group may be attached to the remainder of the molecule at any heteroatom or carbon atom of the ring or ring system. Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like. Exemplary bicyclic heterocyclic groups include indolyl, isoindolyl, benzothiazolyl, benzoxazolyl, benzoxadiazolyl, benzothienyl, benzo[d][1,3]dioxolyl, 2,3-dihydrobenzo[b][1,4]dioxinyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl], or furo[2,3-b]pyridinyl), dihydroisoindolyl, dihydroquinazolinyl (such as 3,4-dihydro-4-oxo-quinazolinyl), triazinylazepinyl, tetrahydroquinolinyl, and the like. Exemplary tricyclic heterocyclic groups include carbazolyl, benzidolyl, phenanthrolinyl, acridinyl, phenanthridinyl, xanthenyl, and the like.

"Substituted heterocycle" and "substituted heterocyclic" (such as "substituted heteroaryl") refer to heterocycle or heterocyclic groups substituted with one or more substituents, preferably 1 to 4 substituents, at any available point of attachment. Exemplary substituents include but are not limited to one or more of the following groups: hydrogen, halogen (e.g., a single halogen substituent or multiple halo substituents forming, in the latter case, groups such as $CF_3$ or an alkyl group bearing $CCl_3$), cyano, nitro, oxo (i.e., =O), $CF_3$, $OCF_3$, cycloalkyl, alkenyl, cycloalkenyl, alkynyl, heterocycle, aryl, $OR_a$, $SR_a$, $S(=O)R_e$, $S(=O)_2R_e$, $P(=O)_2R_e$, $S(=O)_2OR_e$, $P(=O)_2OR_e$, $NR_bR_c$, $NR_bS(=O)_2R_e$, $NR_bP(=O)_2R_e$, $S(=O)_2NR_bR_c$, $P(=O)_2NR_bR_c$, $C(=O)OR_d$, $C(=O)R_a$, $C(=O)NR_bR_c$, $OC(=O)R_a$, $OC(=O)NR_bR_c$, $NR_bC(=O)OR_e$, $NR_dC(=O)NR_bR_c$, $NR_bS(=O)_2NR_bR_c$, $NR_dP(=O)_2NR_bR_e$, $NR_bC(=O)R_a$, or $NR_bP(=O)_2R_e$, wherein each occurrence of $R_a$ is independently hydrogen, alkyl, cycloalkyl, alkenyl, cycloalkenyl, alkynyl, heterocycle, or aryl; each occurrence of $R_b$, $R_c$, and Rd is independently hydrogen, alkyl, cycloalkyl, heterocycle, aryl, or said $R_b$ and $R_e$ together with the N to which they are bonded optionally form a heterocycle; and each occurrence of $R_e$ is independently alkyl, cycloalkyl, alkenyl, cycloalkenyl, alkynyl, heterocycle, or aryl. The exemplary substituents can themselves be optionally substituted. Exemplary substituents also include spiro-attached or fused cyclic substituents at any available point or points of attachment, especially spiro-attached cycloalkyl, spiro-attached cycloalkenyl, spiro-attached heterocycle (excluding heteroaryl), fused cycloalkyl, fused cycloalkenyl, fused heterocycle, or fused aryl, where the aforementioned cycloalkyl, cycloalkenyl, heterocycle, and aryl substituents can themselves be optionally substituted.

The term "alkylamino" refers to a group having the structure —NHR', wherein R' is hydrogen, alkyl or substituted alkyl, or cycloalkyl or substituted cyclolakyl, as defined herein. Examples of alkylamino groups include, but are not limited to, methylamino, ethylamino, n-propylamino, iso-propylamino, cyclopropylamino, n-butylamino, tert-butylamino, neopentylamino, n-pentylamino, hexylamino, cyclohexylamino, and the like.

The term "dialkylamino" refers to a group having the structure —NRR', wherein R and R' are each independently alkyl or substituted alkyl, cycloalkyl or substituted cycloalkyl, cycloalkenyl or substituted cyclolalkenyl, aryl or substituted aryl, or heterocylyl or substituted heterocyclyl, as defined herein. R and R' may be the same or different in a dialkyamino moiety. Examples of dialkylamino groups include, but are not limited to, dimethylamino, methyl ethylamino, diethylamino, methylpropylamino, di(n-propyl)amino, di(iso-propyl)amino, di(cyclopropyl)amino, di(n-butyl)amino, di(tert-butyl)amino, di(neopentyl)amino, di(n-pentyl)amino, di(hexyl)amino, di(cyclohexyl)amino, and the like. In certain embodiments, R and R' are linked to form a cyclic structure. The resulting cyclic structure may be aromatic or non-aromatic. Examples of cyclic diaminoalkyl groups include, but are not limited to, aziridinyl, pyrrolidinyl, piperidinyl, morpholinyl, pyrrolyl, imidazolyl, 1,3,4-trianolyl, and tetrazolyl.

The terms "halogen" or "halo" refer to chlorine, bromine, fluorine, or iodine.

Unless otherwise indicated, any heteroatom with unsatisfied valences is assumed to have hydrogen atoms sufficient to satisfy the valences.

The compounds of the present invention may form salts which are also within the scope of this invention. Reference to a compound of the present invention is understood to include reference to salts thereof, unless otherwise indicated. The term "salt(s)," as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound described herein with an amount of acid or base, such as an equivalent amount, in a medium such as one in which the salt precipitates or in an aqueous medium followed by lyophilization.

The compounds of the present invention which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentane propionates, digluconates, dodecylsulfates, ethanesulfonates, fumarates, glucoheptanoates, glycerophosphates, hemisulfates, heptanoates, hexanoates, hydrochlorides, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates, tartrates, thiocyanates, toluenesulfonates such as tosylates, undecanoates, and the like.

The compounds of the present invention which contain an acidic moiety, such but not limited to a carboxylic acid, may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glycamides, t-butyl amines, and salts with amino acids such as arginine, lysine, and the like. Basic nitrogen-containing groups may be quaternized with agents such as lower alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), aralkyl halides (e.g., benzyl and phenethyl bromides), and others.

Prodrugs and solvates of the compounds of the invention are also contemplated herein. The term "prodrug" as employed herein denotes a compound that, upon administration to a subject, undergoes chemical conversion by metabolic or chemical processes to yield a compound as described herein, or a salt and/or solvate thereof. Solvates of the compounds of the present invention include, for example, hydrates. In certain embodiments, the compound as described herein may be a prodrug itself and, upon administration to a subject, undergoes chemical conversion by metabolic or chemical processes to yield a compound or a salt and/or solvate thereof having desirable biological activities.

Compounds of the present invention, and salts or solvates thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the International Union of Pure and Applied Chemistry (IUPAC) 1974 Recommendations. The racemic forms can be resolved by physical methods, such as, for example, fractional crystallization, separation or crystallization of diastereomeric derivatives, or separation by chiral column chromatography. The individual optical isomers can be obtained from the racemates by any suitable method, including without limitation, conventional methods, such as, for example, salt formation with an optically active acid followed by crystallization.

Compounds of the present invention are, subsequent to their preparation, preferably isolated and purified to obtain a composition containing an amount by weight equal to or greater than 90%, for example, equal to greater than 95%, equal to or greater than 99% of the compounds ("substantially pure" compounds), which is then used or formulated as described herein. Such "substantially pure" compounds of the present invention are also contemplated herein as part of the present invention.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclic rings.

Throughout the specification, groups and substituents thereof may be chosen to provide stable moieties and compounds.

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in "Organic Chemistry," Thomas Sorrell, University Science Books, Sausalito (1999), the entire contents of which are incorporated herein by reference.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Isomeric mixtures containing any of a variety of isomer ratios may be utilized in accordance with the present invention. For example, where only two isomers are combined, mixtures containing 50:50, 60:40, 70:30, 80:20, 90:10, 95:5, 96:4, 97:3, 98:2, 99:1, or 100:0 isomer ratios are all contemplated by the present invention. Those of ordinary skill in the art will readily appreciate that analogous ratios are contemplated for more complex isomer mixtures.

The present invention also includes isotopically-labeled compounds, which are identical to the compounds disclosed herein, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine, and chlorine, such as $^2$H, $^3$H, $^{13}$C, $^{11}$C, $^{14}$C, $^{15}$N, $^{18}$O, $^{17}$O, $^{31}$P, $^{32}$P, S, $^{18}$F, and $^{36}$Cl, respectively. Compounds of the present invention, or an enantiomer, diastereomer, tautomer, or pharmaceutically acceptable salt or solvate thereof, which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and hence, may be preferred in some circumstances. Isotopically labeled compounds can generally be prepared by carrying out the procedures disclosed in the Schemes and/or in the Examples below, by substituting a readily-available isotopically labeled reagent for a non-isotopically labeled reagent.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically active acid or base, followed by resolution of the diastereomers thus formed by fractional crystallization or chromatographic means well known in the art, and subsequent recovery of the pure enantiomers.

It will be appreciated that the compounds, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic, substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds. Combinations of substituents and variables envisioned by this invention are preferably those that result in the formation of stable compounds useful in the treatment, for example, of infectious diseases or proliferative disorders. The term "stable," as used herein, preferably refers to compounds which possess stability sufficient to allow manufacture and which maintain the integrity of the compound for a sufficient period of time to be detected and preferably for a sufficient period of time to be useful for the purposes detailed herein.

As used herein, the term inhibitor of STAT3 as used herein refers to one or more molecules that interfere at least in part with the activity of STAT3 to perform one or more activities, including the ability of STAT3 to bind to a molecule and/or the ability to be phosphorylated.

As used herein, the term "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the terms "cancer" and equivalently, "tumor" refer to a condition in which abnormally replicating cells of host origin are present in a detectable amount in a subject. The cancer can be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric (stomach) cancer; intraepithelial neoplasms; leukemias; lymphomas; liver cancer; lung cancer (e.g., small cell and non-small cell); melanoma; neuroblastomas; oral cancer; ovarian cancer; pancreatic cancer; prostate cancer; rectal cancer; renal (kidney) cancer; sarcomas; skin cancer; testicular cancer; and thyroid cancer; as well as other carcinomas and sarcomas. Cancers can be primary or metastatic.

As used herein, the term "at risk for having cancer" is used herein to refer to patients that have a chance to have cancer because of past, present, or future factors. These factors can include but are not limited to: patient history, family history, identification of markers of generic or tissue-specific cancer such as BRACA-1 or CEA, age, race, diet, being a smoker, or certain exposures such as chemical or radiation exposure.

As used herein, the term "at risk for having muscle wasting" as used herein refers to an individual that is at risk for having less than their normal level of strength or too little muscle or having loss in muscle, such as an individual that has an underlying medical condition with such a symptom, or is elderly.

As used herein, the term "at risk for having cachexia" is used herein to refer to individuals that have a chance to have cachexia because of past, present, or future factors. In particular embodiments, an individual at risk for having cachexia is one that has an underlying condition that is known to cause or be associated with cachexia as at least one symptom. The condition may or may not be chronic. In some embodiments, an underlying medical condition that is known to have cachexia as at least one symptom includes at least renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, myositis, polymyositis, dematomyosytis, rheumatological diseases, autoimmune disease, collagen-vascular disease, visceral leishmaniasis, prolonged bed rest, and/or addiction to drugs, such as amphetamine, opiates, or barbiturates.

As used herein, the term "at risk for having fibrosis" is used herein to refer to individuals that have a chance to have fibrosis because of past, present, or future factors.

As used herein, the term "mammal" is an appropriate subject for the method of the present invention. A mammal may be any member of the higher vertebrate class Mammalia, including humans; characterized by live birth, body hair, and mammary glands in the female that secrete milk for feeding the young. Additionally, mammals are characterized by their ability to maintain a constant body temperature despite changing climatic conditions. Examples of mammals are humans, cats, dogs, cows, mice, rats, and chimpanzees. Mammals may be referred to as "patients" or "subjects" or "individuals."

As used herein, "effective amount" refers to any amount that is necessary or sufficient for achieving or promoting a desired outcome. In some instances, an effective amount is a therapeutically effective amount. A therapeutically effective amount is any amount that is necessary or sufficient for promoting or achieving a desired biological response in a subject. The effective amount for any particular application can vary depending on such factors as the disease or condition being treated, the particular agent being administered, the size of the subject, or the severity of the disease or condition. One of ordinary skill in the art can empirically determine the effective amount of a particular agent without necessitating undue experimentation.

Compounds

In one aspect, a compound of Formula I,

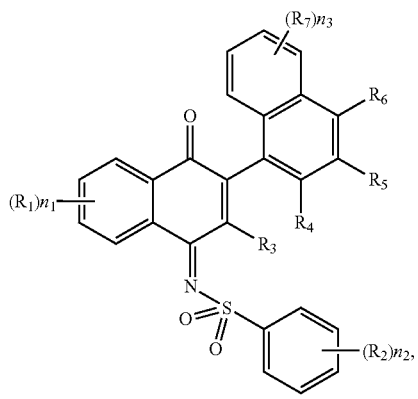

I or a pharmaceutically acceptable salt thereof is described, wherein each occurrence of $R_1$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_1$ is 0, 1, 2, 3, or 4;

each occurrence of $R_2$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(O)NR_bR_c$, $NR_bC(=O)OR_c$, $OC(=O)NR_bR_c$, $NRC(=O)NR_bR_c$, alkyl, alkenyl, cycloalkyl, cycloalkenyl, optionally substituted aryl, optionally substituted aryloxyl, or optionally substituted heterocycle;

$n_2$ is 0, 1, 2, 3, 4, or 5;

$R_3$ is hydrogen, halogen, cyano, nitro, $CF_3$, $OCF_3$, $OR_a$, $SR_a$, $OC(=O)R_a$, alkyl, alkenyl, cycloalkyl, or optionally substituted aryl or heteroaryl;

$R_4$ is hydrogen, halogen, cyano, nitro, $CF_3$, $OCF_3$, $OR_a$, $SR_a$, $NR_bR_c$, $OC(=O)R$, alkyl, alkenyl, or cycloalkyl;

each occurrence of $R_5$, $R_6$, and $R_7$ is independently hydrogen, halogen, cyano, nitro, $CF_3$, $OCF_3$, $OR_a$, $SR_a$, $C(=O)R_a$, $OC(=O)R_a$, $C(=O)OR_a$, $NR_bR_c$, $NR_bC(=O)R_c$, $C(=O)NR_bR_c$, $NR_bC(=O)OR_c$, $OC(=O)NR_bR_c$, $NR_aC(=O)NR_bR_c$, alkyl, alkenyl, cycloalkyl, optionally substituted aryl, or optionally substituted heterocycle;

$n_3$ is 0, 1, 2, 3, or 4; and each occurrence of $R_a$, $R_b$, and $R_c$ is independently hydrogen, alkyl, cycloalkyl, alkenyl, cycloalkenyl, alkynyl, heterocycle, or aryl; or said $R_b$ and $R_c$ together with the nitrogen atom to which they are bonded optionally form a heterocycle comprising 1-4 heteroatoms.

In some embodiments, each occurrence of $R_1$ is independently hydrogen, halogen, cyano, nitro, $CF_3$, $OCF_3$, $OR_a$, or $SR_a$. In some embodiments, each occurrence of $R_1$ is independently $C(=O)R$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_c$, or $NR_aC(=O)NR_bR_c$. In some embodiments, each occurrence of $R_1$ is independently alkyl, alkenyl, cycloalkyl, optionally substituted aryl, or optionally substituted heterocycle. In some embodiments, $R_1$ is H, Me, Et, Pr, i-Pr, Bu, or i-Bu. In some embodiments, $R_1$ is H, OH, SH, $NH_2$, $CF_3$, or $OCF_3$. In some embodiments, $R_1$ is H.

In some embodiments, $n_1$ is 0, 1, or 2. In some embodiments, $n_1$ is 1. In some embodiments, $n_1$ is 0. In some particular embodiments, $R_1$ is H and $n_1$ is 0.

In some embodiments, each occurrence of $R_2$ is independently hydrogen, halogen, cyano, nitro, $CF_3$, $OCF_3$, $OR_a$, or $SR_a$. In some embodiments, each occurrence of $R_2$ is independently $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_e$, or $NR_aC(=O)NR_bR_c$. In some embodiments, each occurrence of $R_2$ is independently alkyl, alkenyl, cycloalkyl, optionally substituted aryl, or optionally substituted heterocycle. In some embodiments, $R_2$ is H, Me, Et, Pr, i-Pr, Bu, or i-Bu. In some embodiments, $R_2$ is H, OH, SH, $NH_2$, $CF_3$, or $OCF_3$. In some embodiments, $R_2$ is H.

In some embodiments, $R_1$ and $R_2$ are both H.

In some embodiments, $n_2$ is 0, 1, or 2. In some embodiments, $n_2$ is 1. In some embodiments, $n_2$ is 0. In some particular embodiments, $R_2$ is H and $n_2$ is 0.

In some embodiments, $R_3$ is hydrogen, halogen, cyano, nitro, or $CF_3$. In some embodiments, $R_3$ is $OCF_3$, $OR_a$, $SR_a$, or $OC(=O)R_a$. In some embodiments, $R_3$ is alkyl, alkenyl, or cycloalkyl. In some embodiments, $R_1$ is H, Me, Et, Pr, i-Pr, Bu, or i-Bu. In some embodiments, $R_3$ is H.

In some embodiments, $R_4$ is hydrogen, halogen, cyano, nitro, or $OR_a$. In some embodiments, $R_4$ is $OCF_3$, $SR_a$, or $OC(=O)R_a$. In some embodiments, $R_4$ is alkyl, alkenyl, or cycloalkyl. In some embodiments, $R_4$ is H, Me, Et, Pr, i-Pr, Bu, or i-Bu. In some embodiments, $R_2$ is H, OH, SH, $NH_2$, $CF_3$, or $OCF_3$. In some embodiments, $R_4$ is OH.

In some embodiments, $R_5$ is selected from the group consisting of hydrogen, halogen, cyano, nitro, and $CF_3$. In some embodiments, $R_5$ is selected from the group consisting of $OCF_3$, $OR_a$, and $SR_a$. In some embodiments, $R_5$ is selected from the group consisting of $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_c$, and $NR_aC(=O)NR_bR_c$. In some embodiments, $R_5$ is selected from the group consisting of alkyl, alkenyl, cycloalkyl, optionally substituted aryl, and optionally substituted heterocycle. In some embodiments, $R_5$ is H, Me, Et, Pr, i-Pr, Bu, or i-Bu. In some embodiments, $R_5$ is H, OH, SH, $NH_2$, $CF_3$, or $OCF_3$. In some embodiments, $R_5$ is H.

In some embodiments, $R_6$ is selected from the group consisting of hydrogen, halogen, cyano, nitro, and $CF_3$. In some embodiments, $R_6$ is selected from the group consisting of $OCF_3$, $OR_a$, and $SR_a$. In some embodiments, $R_6$ is selected from the group consisting of $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_c$, and $NR_aC(=O)NR_bR_c$. In some embodiments, $R_6$ is selected from the group consisting of alkyl, alkenyl, cycloalkyl, optionally substituted aryl, and optionally substituted heterocycle. In some embodiments, $R_6$ is H, Me, Et, Pr, i-Pr, Bu, or i-Bu. In some embodiments, $R_6$ is H, OH, SH, $NH_2$, $CF_3$, or $OCF_3$. In some embodiments, $R_6$ is H.

In some embodiments, each occurrence of $R_7$ is independently selected from the group consisting of hydrogen, halogen, cyano, nitro, and $CF_3$. In some embodiments, each occurrence of $R_7$ is independently selected from the group consisting of $OCF_3$, $OR_a$, and $SR_a$. In some embodiments, each occurrence of $R_7$ is independently selected from the group consisting of $C(=O)R_a$, $OC(=O)R_a$, $C(=O)OR_a$, $NR_aR_b$, $NR_bC(=O)R_a$, $C(=O)NR_bR_c$, $NR_bC(=O)OR_a$, $OC(=O)NR_bR_e$, and $NR_aC(=O)NR_bR_c$. In some embodiments, each occurrence of $R_7$ is independently selected from the group consisting of alkyl, alkenyl, cycloalkyl, optionally substituted aryl, and optionally substituted heterocycle. In some embodiments, each occurrence of $R_7$ is independently H, Me, Et, Pr, i-Pr, Bu, or i-Bu. In some embodiments, each occurrence of $R_7$ is independently H, OH, SH, $NH_2$, $CF_3$, or $OCF_3$. In some embodiments, $R_7$ is H.

In some embodiments, each occurrence of $R_5$, $R_6$, and $R_7$ is H.

In some embodiments, $n_3$ is 0, 1, or 2. In some embodiments, $n_3$ is 1. In some embodiments, $n_3$ is 0.

In some embodiments, each occurrence of $R_a$ is independently hydrogen, alkyl, heterocycle, or aryl. In some embodiments, each occurrence of R is independently hydrogen or alkyl. In some embodiments, each occurrence of $R_a$ is independently H, Me, Et, Pr, i-Pr, Bu, or i-Bu.

In some embodiments, each occurrence of $R_b$ and $R_e$ is independently hydrogen, alkyl, heterocycle, or aryl. In some embodiments, each occurrence of $R_b$ and $R_e$ is independently hydrogen or alkyl.

In other embodiments, $R_b$ and $R_e$ together with the nitrogen atom to which they are bonded optionally form a heterocycle comprising 1-4 heteroatoms each selected from the group consisting of N, O, and S. In other embodiments, $R_b$ and $R_e$ together with the nitrogen atom to which they are bonded form optionally substituted morpholine, piperidine, or piperazine.

In some embodiments, the compound has the structure of Formula II:

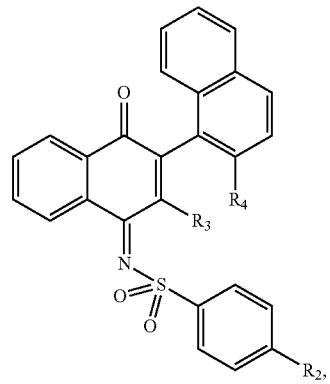

II or a pharmaceutically acceptable salt thereof.

In some embodiments, $R_2$ is H, OH, alkyl, alkoxy, halogen, $NR_bR_e$, $CF_3$, $OCF_3$, or CN. In some embodiments, $R_2$ is $NH_2$, OH, OMe, OEt, $OCH_2CH_2CH_3$, or $OCH(CH_3)_2$. In some embodiments, $R_2$ is selected from the group consisting of hydrogen, methyl, ethyl, propyl, tert-butyl, F, Cl, Br, $CF_3$, nitro, OMe, OEt, $OCF_3$, —C(=O)Me, —C(=O)OMe, —NHC(=O)Me, 1,4-dioxanyl, cyclohexanyl, cyclohexenyl, phenoxy, 2-methoxyphenoxy, 3-methoxyphenoxy, 4-methoxyphenoxy, 2-chlorophenoxy, 3-chlorophenoxy, 4-chlorophenoxy, 2-methylphenoxy, 3-methylphenoxy, and 4-methylphenoxy. In some embodiments, $R_2$ is OMe, OEt, OPr, OBu, or O-iBu. In some embodiments, $R_2$ is OMe.

In some embodiments, $R_3$ is H, OH, alkyl, alkoxy, or halogen. In some embodiments, $R_3$ is H, Me, Et, Pr, i-Pr, Bu, or i-Bu. In some embodiments, $R_3$ is H.

In some embodiments, $R_4$ is H, alkyl, OH, $NH_2$, alkoxy, halogen, $CF_3$, or CN. In some embodiments, $R_4$ is H, OH, or alkoxy. In some embodiments, $R_4$ is OH. In some embodiments, $R_4$ is H.

In some embodiments, the compound has the structure of Formula III,

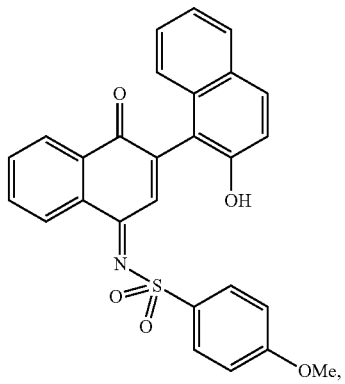

III or a pharmaceutically acceptable salt thereof.

In some embodiments, the compound of Formula I is selected from the Examples of compounds shown in Table 1a, or a pharmaceutically acceptable salt thereof. The enumerated compounds in Table 1a are representative and non-limiting examples of compounds of Formula I.

TABLE 1a

Selected compound of Formula I, where $n_1$, $n_2$, and $n_3$ are independently 1 or 2.

| Example No. | R₁ | R₂ | R₃ | R₄ |
|---|---|---|---|---|
| 100 | H | Cl | H | H |
| 102 | F | H | F | H |
| 103 | Cl | 1,4-dimethylpiperazinyl | Cl | OH |
| 104 | CN | OH | CN | OH |
| 105 | NO₂ | OMe | CF₃ | OH |
| 106 | CF₃ | OEt | Me | OMe |
| 107 | OCF₃ | OPr | Et | NH₂ |
| 108 | OH | OBu | Pr | NH₂ |
| 109 | OH | NH₂ | Bu | NH₂ |
| 110 | SH | SH | Cyclopropyl | SH |
| 111 | COOH | Me | H | SCH₃ |
| 112 | COOMe | CONH₂ | H | COOH |
| 113 | CONH₂ | NH(C=O)Me | —CH=CH₂ | COOH |
| 114 | CONMe₂ | cyclopropyl | Ph | OH |
| 115 | NH(C=O)Me | Ph | pyridinyl | OH |
| 116 | Me | 3-fluorophenyl | Me | OH |
| 117 | Ph | 4-pyridinyl | H | NHMe |
| 118 | 4-chlorophenyl | NO₂ | H | NHMe |
| 119 | 1,4-dimethylpiperazinyl | CF₃ | H | NMe₂ |
| 120 | cyclobutyl | OH | H | 1-methylpyrrolidinyl |
| 121 | 4-pyridinyl | SH | H | 1,4-dimethylpiperazinyl |
| 122 | OEt | Me | Me | Me |
| 123 | OPr | Et | Ph | Me |
| 124 | OBu | Pr | Ph | Et |

| Example No. | R₅ | R₆ | R₇ |
|---|---|---|---|
| 100 | H | F | F |
| 102 | F | OH | Cl |
| 103 | Cl | OH | NO₂ |
| 104 | Br | OMe | OCF₃ |
| 105 | NO₂ | NH₂ | SH |
| 106 | OCF₃ | NH₂ | SH |
| 107 | OCF₃ | SCH₃ | OH |
| 108 | SH | COOH | CONH₂ |
| 109 | SH | COOH | CONH₂ |
| 110 | OH | Ph | OH |
| 111 | OH | pyridinyl | OH |
| 112 | CONH₂ | Ph | OH |
| 113 | CONH₂ | Me | H |
| 114 | CONH₂ | Et | H |
| 115 | NH(C=O)Me | Pr | Me |
| 116 | Me | cyclobutyl | Et |
| 117 | Et | CF₃ | cyclopropyl |
| 118 | cyclobutyl | OCF₃ | NO₂ |
| 119 | 4-chlorophenyl | SH | pyridinyl |
| 120 | Ph | Ph | 4-pyridinyl |
| 121 | OEt | 4-chlorophenyl | CONMe₂ |
| 122 | OPr | OPr | NH(C=O)Me |

TABLE 1a-continued

Selected compound of Formula I, where $n_1$, $n_2$, and $n_3$ are independently 1 or 2.

| 123 | (N-methylpiperazinyl) | (pyrrolidinyl) | (N-methylpiperazinyl) |
| 124 | (N-methylpiperazinyl) | (pyrrolidinyl) | (morpholinyl) |

In some embodiments, the compound of Formula II is selected from the Examples of compounds shown in Table 1b, or a pharmaceutically acceptable salt thereof. The enumerated compounds in Table 1b are representative and non-limiting examples of compounds of Formula II.

TABLE 1b

Selected compound of Formula II.

| Example No. | $R_2$ | $R_3$ | $R_4$ |
|---|---|---|---|
| 125 | Cl | H | H |
| 126 | H | F | OH |
| 127 | (N-methylpiperazinyl) | Cl | OH |
| 128 | OH | H | OH |
| 129 | OMe | $CF_3$ | OH |
| 130 | OEt | Me | OMe |
| 131 | OPr | Et | $NH_2$ |
| 132 | OBu | Pr | $NH_2$ |
| 133 | $NH_2$ | Bu | $NH_2$ |
| 134 | SH | cyclopropyl | SH |
| 135 | Me | H | $SCH_3$ |
| 136 | $CONH_2$ | H | COOH |
| 137 | NH(C=O)Me | —CH=$CH_2$ | COOH |
| 138 | cyclopropyl | Ph | OH |
| 139 | Ph | pyridinyl | OH |
| 140 | 3-fluorophenyl | Me | OH |
| 141 | 4-pyridinyl | H | NHMe |
| 142 | $NO_2$ | H | NHMe |
| 143 | $CF_3$ | H | $NMe_2$ |
| 144 | OH | H | (pyrrolidinyl) |
| 145 | SH | H | (N-methylpiperazinyl) |
| 146 | Me | Me | Me |
| 147 | Et | Ph | Me |
| 148 | Pr | Ph | Et |

Methods of Preparation

Abbreviations

ACN Acetonitrile
EA Ethyl acetate
DMF Dimethyl formamide
PE Petroleum ether
DCM Dichloromethane
THF Tetrahydrofuran
HOBT 1-Hydroxybenzotriazole
EDCI 1-Ethyl-3-(3-dimethylaminopropyl)carbodiimide
HBTU 2-(1H-Benzotriazole-1-yl)-1,1,3,3-tetramethyluronium hexafluorophosphate
HATU N-[(dimethylamino)(3H-1,2,3-triazolelo(4,4-b)pyridin-3-yloxy)methylene]-N-methylmethaneaminium hexafluorophosphate
PyBOP 1H-Benzotriazol-1-yloxytripyrrolidinophosphoniumhexafluorophosphate
BOPCl Bis(2-oxo-3-oxazolidinyl)phosphinic chloride
BOP Benzotriazol-1-yloxytris(diethylamino)phosphonium hexafluorophosphate
TEA Triethylamine
DIPEA Diisopropylethylamine
DMAP 4-Dimethylaminopyridine
PCC Pyridinium chlorochromate
PDC Pyridinium dichromate
NBS N-bromosuccinimide
NCS N-chlorosuccinimide
NIS N-iodosuccinimide
9-BBN 9-Borabicyclo[3.3.1]nonane
TsOH p-Toluenesulfonic acid
TFA Trifluoroacetamide
CDI Carbonyldiimidazole Following are general synthetic schemes for manufacturing compounds of the present invention. These schemes are illustrative and are not meant to limit the possible techniques one skilled in the art may use to manufacture the compounds disclosed herein. Different methods will be evident to those skilled in the art. Additionally, the various steps in the synthesis may be performed in an alternate sequence or order to give the desired compound(s). The following reactions are illustrations but not limitations of the preparation of some of the starting materials and compounds disclosed herein.

Schemes 1-4 below describe which may be used for the synthesis of compounds having the structure of Formula I, where $R_1$, $R_2$, $R_3$, $R_4$, $R_5$, $R_6$, $R_7$, $n_1$, $n_2$, and $n_3$ are defined according to any one of the embodiments disclosed herein. Because compounds of Formulae II and III are encompassed by Formula I, these compounds can be prepared using the same methods described in Schemes 1-4. Various modifications to these methods may be envisioned by those skilled in the art to achieve similar results given below. The starting materials and reagents used in the method described in Schemes 1-4 are commercially available or can be prepared by methods known in the art. The reactions described in Schemes 1-4 may be carried out at low temperature (e.g., 0° C.), room temperature, or under heating conditions (e.g., at 50, 60, 70, 80, 90 or 100° C. or at the refluxing temperature of the solvent used).

Scheme 1

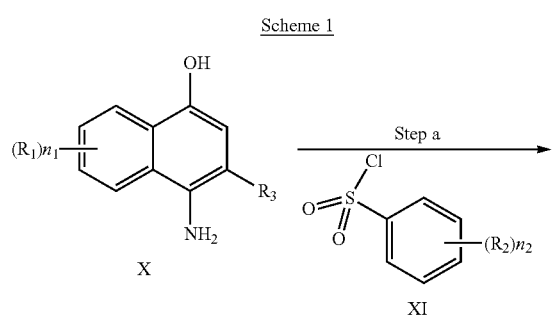

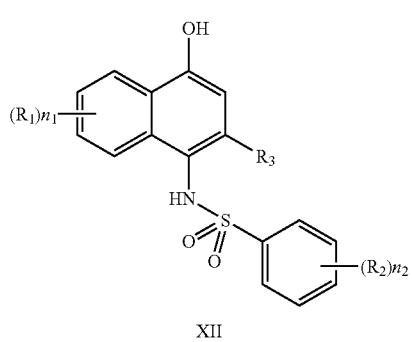

In certain embodiments, as shown in Scheme 1, Step a, aminonaphthelene X is reacted with phenylsulfonyl chloride XI to afford sulfonamide XII. Other than aminonaphthelene X, any salt of aminonaphthelene X can be used as starting material as well. Non-limiting examples of the salts include HCl, $H_2SO_4$, $HNO_3$, or HAc salt or any other salts known in the art. Any suitable base, organic or inorganic, may be used in step a. Non-limiting examples of suitable bases include $CH_3COONa$, $Na_2CO_3$, $K_2CO_3$, NaOH, KOH, CsOH, sodium hydride, potassium carbonate, triethylamine, and diisopropylethylamine. Non-limiting example of suitable solvents for this reaction include DMSO, ethanol, water, THF, methylene chloride, acetonitrile, chloroform, or toluene.

Scheme 2

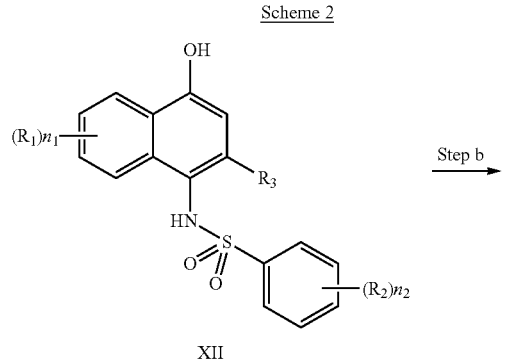

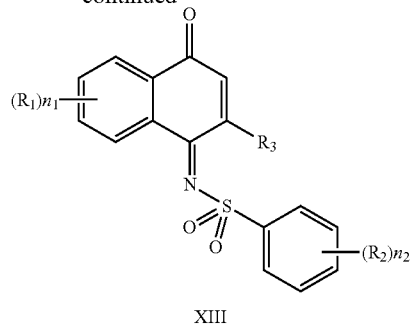

In certain embodiments, as shown in Step b in Scheme 2, the obtained sulfonamide XII is oxidized using one or more oxidation agents to afford iminonaphthalenone XIII. Non-limiting examples of suitable oxidation agents for this reaction include $NaIO_4$, $H_2O_2$, and MCPBA. Non-limiting examples of suitable solvents for this reaction include DMSO, ethanol, water, THF, methylene chloride, acetonitrile, chloroform, or toluene.

Scheme 3

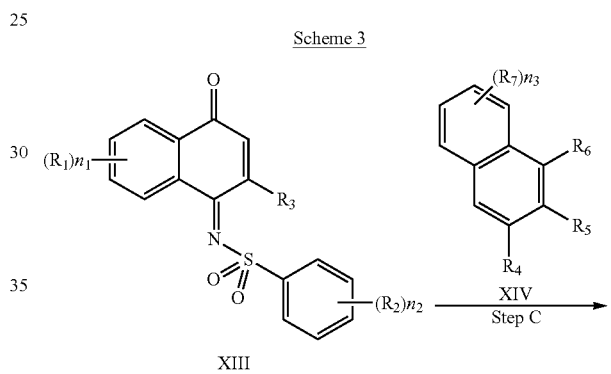

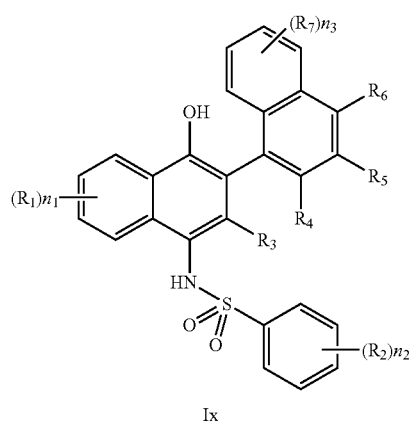

In certain embodiments, as shown in Step c in Scheme 3, the obtained iminonaphthalenone XIII is coupled with naphthalene XIV to afford compound of Formula Ix. One or more lewis acids may be used to facilitate this coupling reaction. Non-limiting examples of suitable lewis acids for this reaction include $BF_3$, $FeCl_2$, $FeCl_3$, $CuCl_2$, and $AlCl_3$. Non-limiting examples of suitable solvents for this reaction include DMSO, ethanol, water, TH, methylene chloride, acetonitrile, chloroform, and toluene.

Scheme 4

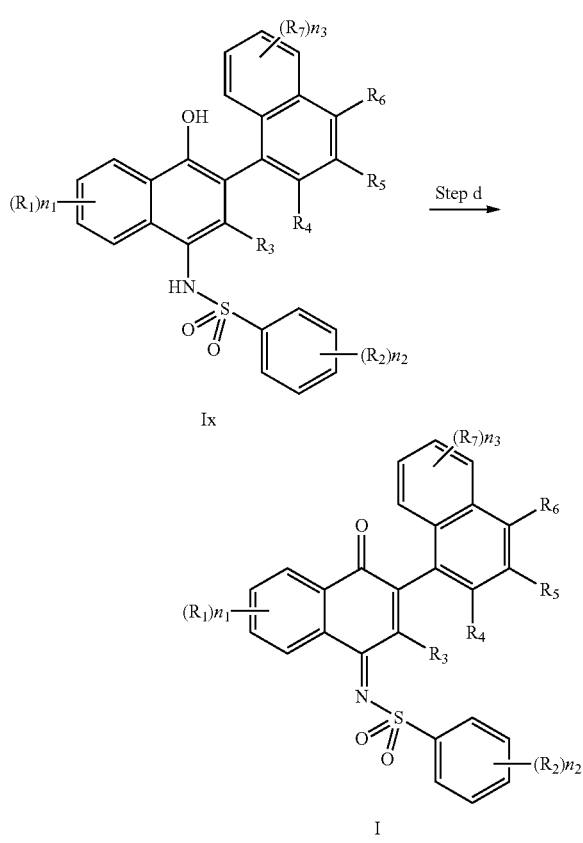

Ix

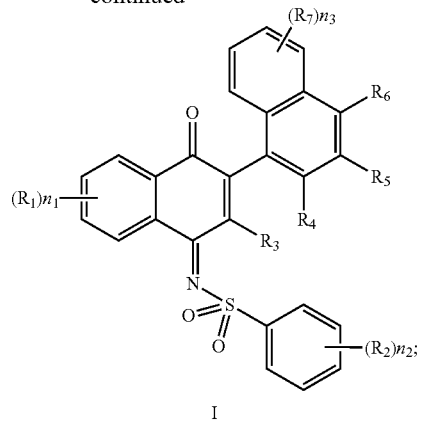

I

In certain embodiments, as shown in Step d in Scheme 4, the obtained compound of Formula Ix is oxidized using one or more oxidation agents to afford compound of Formula I. Non-limiting examples of suitable oxidation agents for this reaction include NaIO$_4$, H$_2$O$_2$, and MCPBA. Non-limiting examples of suitable solvents for this reaction include DMSO, ethanol, water, THF, methylene chloride, acetonitrile, chloroform, or toluene.

Thus, in yet another aspect, a method of making a compound of Formula I is disclosed, including the step of oxidizing a compound of Formula Ix to form the compound of Formula I using an oxidation reagent in step a):

a)

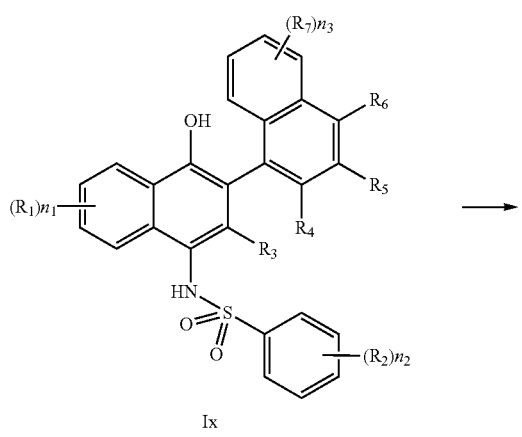

Ix where each occurrence of R$_1$ is independently hydrogen, halogen, cyano, nitro, CF$_3$, OCF$_3$, OR$_a$, SR$_a$, C(=O)R$_a$, OC(=O)R$_a$, C(=O)OR$_a$, NR$_b$R$_c$, NR$_b$C(=O)R$_c$, C(=O)NR$_b$R$_c$, NR$_b$C(=O)OR$_c$, OC(=O)NR$_b$R$_c$, NR$_a$C(=O)NR$_b$R$_c$, alkyl, alkenyl, cycloalkyl, optionally substituted aryl, or optionally substituted heterocycle;

n$_1$ is 0, 1, 2, 3, or 4;

each occurrence of R$_2$ is independently hydrogen, halogen, cyano, nitro, CF$_3$, OCF$_3$, OR$_a$, SR$_a$, C(=O)R$_a$, OC(=O)R$_a$, C(=O)OR$_a$, NR$_b$R$_c$, NR$_b$C(=O)R$_c$, C(=O)NR$_b$R$_c$, NR$_b$C(=O)OR$_c$, OC(=O)NR$_b$R$_c$, NR$_a$C(=O)NR$_b$R$_c$, alkyl, alkenyl, cycloalkyl, cycloalkenyl, optionally substituted aryl, optionally substituted aryloxyl, or optionally substituted heterocycle;

n$_2$ is 0, 1, 2, 3, 4, or 5;

R$_3$ is hydrogen, halogen, cyano, nitro, CF$_3$, OCF$_3$, OR$_a$, SR$_a$, OC(=O)R$_a$, alkyl, alkenyl, cycloalkyl, or optionally substituted aryl or heteroaryl;

R$_4$ is hydrogen, halogen, cyano, nitro, CF$_3$, OCF$_3$, OR$_a$, SR$_a$, NR$_b$R$_c$, OC(=O)R$_a$, alkyl, alkenyl, or cycloalkyl;

each occurrence of R$_5$, R$_6$, and R$_7$ is independently hydrogen, halogen, cyano, nitro, CF$_3$, OCF$_3$, OR$_a$, SR$_a$, C(=O)R$_a$, OC(=O)R$_a$, C(=O)OR$_a$, NR$_b$R$_c$, NR$_b$C(=O)R$_c$, C(=O)NR$_b$R$_c$, NR$_b$C(=O)OR$_c$, OC(=O)NR$_b$R$_c$, NR$_a$C(=O)NR$_b$R$_c$, alkyl, alkenyl, cycloalkyl, optionally substituted aryl, or optionally substituted heterocycle;

n$_3$ is 0, 1, 2, 3, or 4; and each occurrence of R$_a$, R$_b$, and R$_c$ is independently hydrogen, alkyl, cycloalkyl, alkenyl, cycloalkenyl, alkynyl, heterocycle, or aryl; or said R$_b$ and R$_c$ together with the nitrogen atom to which they are bonded optionally form a heterocycle comprising 1-4 heteroatoms.

In some embodiments, the oxidation reagent is selected from the group consisting of NaIO$_4$, H$_2$O$_2$, MCPBA, and a combination thereof. In some specific embodiments, the oxidation reagent is NaIO$_4$. In some embodiments, NaIO$_4$ is prepared in situ.

In some embodiments, the oxidation reagent is used in the amount of about 1.5-4.0 equivalence to the compound of Formula Ix. In some embodiments, the oxidation reagent is used in the amount of about 1.5, 2.0, 2.5, 3.0, 3.5, or 4.0 equivalence to the compound of Formula Ix, or in an equivalence in an range bounded by any two values disclosed herein.

In some embodiments, the oxidation reagent is used in the amount of about 2.0-3.5 equivalence to the compound of Formula Ix. In some embodiments, the oxidation reagent is used in the amount of about 2.5 equivalence to the compound of Formula Ix.

In some embodiments, step a is conducted for about 12 hours to about 2 days. In any one or more of the embodiments described herein, step a is conducted for about 1 day.

In some embodiments, each occurrence of $R_1$ is independently hydrogen, halogen, cyano, nitro, $CF_3$, $OCF_3$, $OR_a$, or $SR_a$.

In some embodiments, each occurrence of $R_1$ is H.

In some embodiments, each occurrence of $R_2$ is independently halogen, cyano, nitro, $CF_3$, $OCF_3$, $OR_a$, or $SR_a$.

In some embodiments, $R_2$ is OMe and $n_2$ is 1.

In some embodiments, $R_3$ is $OCF_3$, $OR_a$, $SR_a$, $OC(=O)R_a$, alkyl, alkenyl, or cycloalkyl. In some embodiments, $R_3$ is H.

In any one or more of the embodiments described herein, the compound of Formula I has the structure of Formula III,

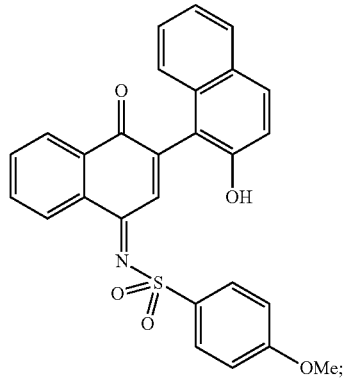

III and the compound of Formula Ix has the structure of Formula IIIx,

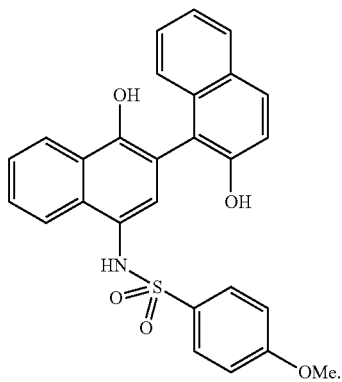

IIIx

Methods of Inhibiting STAT3 and Treatment of a Disorder

In yet another aspect, a method of inhibiting STAT3 in a cell is described, comprising delivering to the cell an effective amount of at least one compound according to any one or more of the embodiments described herein or a pharmaceutically acceptable salt thereof.

In some embodiments, the cell is in vivo in a mammal. In some embodiments, the mammal is a human, a dog, a cat, a horse, a cow, a pig, a sheep, goat, or a Tasmanian devil. In some embodiments, the mammal is a human.

In some embodiments, the cell is a cancer cell. In some embodiments, the method further includes inducing apoptosis in the cancer cell. In some embodiments, the method further includes inhibiting angiogenesis in a tumor, enhancing anti-tumor immune-mediated cytotoxicity, decreasing tumor growth, improving the mammal's survival, inhibiting STAT3 phosphorylation, and/or inhibiting nuclear-to-cytoplasmic translocation of STAT3.

In some embodiments, the human is suffering from, or known, suspected, or at risk for developing anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, astrogliosis due to Alzheimer's or other neurodegenerative disease, or a combination thereof.

In some embodiments, the hyperproliferative disease is selected from the group consisting of head and neck cancer, lung cancer, liver cancer, breast cancer, skin cancer, kidney cancer, testicular cancer, colon cancer, rectal cancer, gastric cancer, metastatic melanoma, prostate cancer, ovarian cancer, cervical cancer, bone cancer, spleen cancer, gall bladder cancer, brain cancer, pancreatic cancer, stomach cancer, anal cancer, prostate cancer, multiple myeloma, post-transplant lymphoproliferative disease, restenosis, myelodysplastic syndrome, and leukemia. In some embodiments, the leukemia is acute myelogenous leukemia.

In some embodiments, the fibrosis is selected from the group consisting of pulmonary fibrosis, bone marrow fibrosis, intestine fibrosis, pancreatic fibrosis, joint fibrosis, liver fibrosis, retroperionteum, myelofibrosis, and dermal fibrosis.

In some embodiments, the viral infection is a chronic viral infection. In some embodiments, the chronic viral infection is AIDS, HIV infection, Hepatitis B virus infection, Hepatitis C virus infection, or Epstein-Barr virus infection.

In some embodiments, the disorder is asthma, psoriasis, inflammatory bowel disease, uveitis, scleritis, multiple sclerosis, graft-versus-host diseases, pancreatitis, pulmonary lymphangioleiomyomatosis, age-related macular degeneration, or amyloidosis. In some embodiments, the anaphylaxis comprises anaphylactic shock.

In some embodiments, the disorder is selected from the group consisting of muscle wasting, muscle weakness, cachexia, and a combination thereof; and the human has or is at risk of having muscle wasting, cachexia, renal failure, cancer, AIDS, HIV infection, chronic obstructive lung disease (including emphysema), multiple sclerosis, congestive heart failure, tuberculosis, familial amyloid polyneuropathy, acrodynia, hormonal deficiency, metabolic acidosis, infectious disease, chronic pancreatitis, autoimmune disorder, celiac disease, Crohn's disease, electrolyte imbalance, Addison's disease, sepsis, burns, trauma, fever, long bone fracture, hyperthyroidism, prolonged steroid therapy, surgery, bone marrow transplant, atypical pneumonia, brucellosis, endocarditis, Hepatitis B, lung abscess, mastocytosis, paraneoplastic syndrome, polyarteritis nodosa, sarcoidosis, systemic lupus erythematosus, visceral leishmaniasis, prolonged bed rest, or drug addiction. In some embodiments, the chronic obstructive lung disease is emphysema.

In yet another aspect, a method of treating or preventing a disorder in a mammalian species in need thereof is described, comprising administering to the mammalian species a therapeutically effective amount of at least one compound according to any one or more embodiments described herein or a pharmaceutically acceptable salt thereof, wherein the disorder is selected from the group consisting of a neurodegenerative disease, anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, and a combination thereof.

In some embodiments, the mammalian species is a human, a dog, a cat, a horse, a cow, a pig, a sheep, or a goat. In some embodiments, the mammalian species is a human. In some embodiments, the human is suffering from, at risk of having, or susceptible to have a disorder.

In any one or more of the embodiments described herein, the disorder is selected from the group consisting of a neurodegenerative disease, anaphylaxis, muscle wasting, muscle weakness, cachexia, asthma, ulcerative colitis, non-alcoholic fatty liver disease, fibrosis, steatohepatitis, chagasic cardiomyopathy, scleroderma, a hyperproliferative disease, a viral infection, myelodysplastic syndrome, asthma, psoriasis, inflammatory bowel disease, uveitis, scleritis, multiple sclerosis, graft-versus-host diseases, pancreatitis, pulmonary lymphangioleiomyomatosis, age-related macular degeneration, amyloidosis, and a combination thereof. In some embodiments, the neurodegenerative disease is chemotherapy-induced peripheral neuropathy, diabetic neuropathy or chemobrain.

Assays for Effectiveness

STAT3 cellular inhibition can be assayed using PY-Stat3 antibodies to measure PY-STAT3 analyze in lysates of cells by luminex beads, immunoblotting, or eliza or in slides of tissue by immunohistochemistry in peripheral blood mononuclear cell and tumor cell lines (kasumi-1) in tumor samples.

The invention will now be further described by the working examples below, which are preferred embodiments of the invention. These examples are illustrative rather than limiting, and it is to be understood that there may be other embodiments that fall within the spirit and scope of the invention as defined by the claims appended hereto.

Pharmaceutical Compositions

This invention also provides a pharmaceutical composition comprising at least one of the compounds as described herein or a pharmaceutically acceptable salt or solvate thereof, and a pharmaceutically acceptable carrier.

In yet another aspect, a pharmaceutical composition is described, comprising at least one compound according to any one or more of the embodiments described herein, e.g., compounds of Formula I, II, or III, or a pharmaceutically acceptable salt thereof, and a pharmaceutically acceptable carrier or diluent.

The phrase "pharmaceutically acceptable carrier" as used herein means a pharmaceutically acceptable material, composition, or vehicle, such as a liquid or solid filler, diluent, excipient, solvent, or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as butylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. The term "carrier" denotes an organic or inorganic ingredient, natural or synthetic, with which the active ingredient is combined to facilitate the application. The components of the pharmaceutical compositions also are capable of being comingled with the compounds of the present invention, and with each other, in a manner such that there is no interaction which would substantially impair the desired pharmaceutical efficiency.

As set out above, certain embodiments of the present pharmaceutical agents may be provided in the form of pharmaceutically acceptable salts. The term "pharmaceutically acceptable salt," in this respect, refers to the relatively non-toxic, inorganic, and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, aurylsulphonate salts, and the like. (See, for example, Berge et al., (1977) "Pharmaceutical Salts,", *J. Pharm. Sci.* 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, butionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups, and thus are capable of forming pharmaceutically acceptable salts with pharmaceutically acceptable bases. The term "pharmaceutically acceptable salts" in these instances refers to the relatively non-toxic, inorganic, and organic base addition salts of compounds of the present invention. These salts can likewise be prepared in situ during the final isolation and purification of the compounds, or by separately reacting the purified compound in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, aluminum salts, and the like. Representative organic amines useful for the formation of base addition salts include ethylamine, diethylamine, ethylenediamine, ethanolamine, diethanolamine, piperazine, and the like. (See, for example, Berge et aL., supra.)

Wetting agents, emulsifiers, and lubricants, such as sodium lauryl sulfate, magnesium stearate, and polyethylene oxide-polybutylene oxide copolymer, as well as coloring agents, release agents, coating agents, sweetening, flavoring and perfuming agents, preservatives, and antioxidants can also be present in the compositions.

Formulations of the present invention include those suitable for oral, nasal, topical (including buccal and sublingual), rectal, vaginal, and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient, which can be combined with a carrier material to produce a single dosage form will generally be that amount of the compound which produces a therapeutic effect. Generally, out of 100%, this amount will range from about 1% to about 99% of active ingredient, preferably from about 5% to about 70%, most preferably from about 10% to about 30%.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely-divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. A compound of the present invention may also be administered as a bolus, electuary, or paste.

In solid dosage forms of the invention for oral administration (capsules, tablets, pills, dragees, powders, granules, and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose, and/or acacia; humectants, such as glycerol; disintegrating agents, such as agar-agar, calcium carbonate, potato or tapioca starch, alginic acid, certain silicates, sodium carbonate, and sodium starch glycolate; solution-retarding agents, such as paraffin; absorption accelerators, such as quaternary ammonium compounds; wetting agents, such as, for example, cetyl alcohol, glycerol monostearate, and polyethylene oxide-polybutylene oxide copolymer; absorbents, such as kaolin and bentonite clay; lubricants, such as talc, calcium stearate, magnesium stearate, solid polyethylene glycols, sodium lauryl sulfate, and mixtures thereof, and coloring agents. In the case of capsules, tablets, and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxybutylmethyl cellulose), lubricant, inert diluent, preservative, disintegrant (for example, sodium starch glycolate or cross-linked sodium carboxymethyl cellulose), surface-active, or dispersing agent. Molded tablets may be made by molding in a suitable machine a mixture of the powdered compound moistened with an inert liquid diluent.

The tablets and other solid dosage forms of the pharmaceutical compositions of the present invention, such as dragees, capsules, pills, and granules, may optionally be scored or prepared with coatings and shells, such as enteric coatings and other coatings well-known in the pharmaceutical-formulating art. They may also be formulated so as to provide slow or controlled release of the active ingredient therein using, for example, hydroxybutylmethyl cellulose in varying proportions to provide the desired release profile, other polymer matrices, liposomes, and/or microspheres. They may be sterilized by, for example, filtration through a bacteria-retaining filter, or by incorporating sterilizing agents in the form of sterile solid compositions, which can be dissolved in sterile water or some other sterile injectable medium immediately before use. These compositions may also optionally contain opacifying agents and may be of a compositions that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups, and elixirs. In addition to the active ingredient, the liquid dosage forms may contain inert diluents commonly used in the art, such as, for example, water or other solvents, solubilizing agents and emulsifiers, such as ethyl alcohol, isobutyl alcohol, ethyl carbonate, ethyl acetate, benzyl alcohol, benzyl benzoate, butylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Additionally, cyclodextrins, e.g., hydroxybutyl-β-cyclodextrin, may be used to solubilize compounds.

Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax, or a salicylate, and which is solid at room temperature, but liquid at body temperature and therefore, will melt in the rectum or vaginal cavity and release the active pharmaceutical agents of the invention.

Formulations of the present invention which are suitable for vaginal administration also include pessaries, tampons, creams, gels, pastes, foams, or spray formulations containing such carriers as are known in the art to be appropriate.

Dosage forms for the topical or transdermal administration of a compound of this invention include powders, sprays, ointments, pastes, creams, lotions, gels, solutions, patches, and inhalants. The active compound may be mixed under sterile conditions with a pharmaceutically acceptable carrier, and with any preservatives, buffers, or propellants which may be required.

The ointments, pastes, creams, and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to a compound of this invention, excipients such as lactose, talc, silicic acid, aluminum hydroxide, calcium silicates, and polyamide powder, or mixtures of these substances. Sprays can additionally contain customary propellants, such as chlorofluorohydrocarbons and volatile unsubstituted hydrocarbons, such as butane.

Transdermal patches have the added advantage of providing controlled delivery of a compound of the present invention to the body. Such dosage forms can be made by dissolving or dispersing the pharmaceutical agents in the proper medium. Absorption enhancers can also be used to increase the flux of the pharmaceutical agents of the invention across the skin. The rate of such flux can be controlled by either providing a rate controlling membrane or dispersing the compound in a polymer matrix or gel.

Ophthalmic formulations, eye ointments, powders, solutions, and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient, or suspending or thickening agents.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. One strategy for depot injections includes the use of polyethylene oxide-polypropylene oxide copolymers wherein the vehicle is fluid at room temperature and solidifies at body temperature.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly (anhydrides). Depot injectable formulations are also prepared by entrapping the drug in liposomes or microemulsions, which are compatible with body tissue.

When the compounds of the present invention are administered as pharmaceuticals to humans and animals, they can be given per se or as a pharmaceutical composition containing, for example, 0.1% to 99.5% (more preferably, 0.5% to 90%) of active ingredient in combination with a pharmaceutically acceptable carrier.

The compounds and pharmaceutical compositions of the present invention can be employed in combination therapies, that is, the compounds and pharmaceutical compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, the compound of the present invention may be administered concurrently with another anti-inflammatory or immunosuppressant agent); such as but not limited to NSAIDS, DMARDS, steroids, or biologics such as antibody therapies), or they may achieve different effects (e.g., control of any adverse effects).

The compounds of the invention may be administered intravenously, intramuscularly, intraperitoneally, subcutaneously, topically, orally, or by other acceptable means. The compounds may be used to treat arthritic conditions in mammals (e.g., humans, livestock, and domestic animals), race horses, birds, lizards, and any other organism which can tolerate the compounds.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use, or sale of pharmaceuticals or biological products, which notice reflects approval by the agency of manufacture, use, or sale for human administration.

Administration to a Subject

Some aspects of the invention involve administering an effective amount of a composition to a subject to achieve a specific outcome. The small-molecule compositions useful according to the methods of the present invention thus can be formulated in any manner suitable for pharmaceutical use.

The formulations of the invention are administered in pharmaceutically acceptable solutions which may routinely contain pharmaceutically acceptable concentrations of salt, buffering agents, preservatives, compatible carriers, adjuvants, and optionally other therapeutic ingredients.

For use in therapy, an effective amount of the compound can be administered to a subject by any mode allowing the compound to be taken up by the appropriate target cells. "Administering" the pharmaceutical composition of the present invention can be accomplished by any means known to the skilled artisan. Specific routes of administration include but are not limited to oral, transdermal (e.g., via a patch), parenteral injection (subcutaneous, intradermal, intramuscular, intravenous, intraperitoneal, intrathecal, etc.), or mucosal (intranasal, intratracheal, inhalation, intrarectal, intravaginal, etc.). An injection can be in a bolus or a continuous infusion.

For example the pharmaceutical compositions according to the invention are often administered by intravenous, intramuscular, or other parenteral means. They can also be administered by intranasal application, inhalation, topically, orally, or as implants, and even rectal or vaginal use is possible. Suitable liquid or solid pharmaceutical preparation forms are, for example, aqueous or saline solutions for injection or inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops, or preparations with protracted release of active compounds, in whose preparation excipients and additives and/or auxiliaries such as disintegrants, binders, coating agents, swelling agents, lubricants, flavorings, sweeteners, or solubilizers are customarily used as described above. The pharmaceutical compositions are suitable for use in a variety of drug delivery systems. For a brief review of present methods for drug delivery, see Langer R (1990) Science 249:1527-33, which is incorporated herein by reference.

The concentration of compounds included in compositions used in the methods of the invention can range from about 1 nM to about 100 µM. Effective doses are believed to range from about 10 picomole/kg to about 100 micromole/kg.

The pharmaceutical compositions are preferably prepared and administered in dose units. Liquid dose units are vials or ampoules for injection or other parenteral administration. Solid dose units are tablets, capsules, powders, and suppositories. For treatment of a patient, depending on activity of the compound, manner of administration, purpose of the administration (i.e., prophylactic or therapeutic), nature and severity of the disorder, age, and body weight of the patient, different doses may be necessary. The administration of a given dose can be carried out both by single administration in the form of an individual dose unit or else several smaller dose units. Repeated and multiple administration of doses at specific intervals of days, weeks, or months apart are also contemplated by the invention.

The compositions can be administered per se (neat) or in the form of a pharmaceutically acceptable salt. When used in medicine, the salts should be pharmaceutically acceptable, but non-pharmaceutically acceptable salts can conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium, or calcium salts of the carboxylic acid group.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v); and thimerosal (0.004-0.02% w/v).

Compositions suitable for parenteral administration conveniently include sterile aqueous preparations, which can be isotonic with the blood of the recipient. Among the acceptable vehicles and solvents are water, Ringer's solution, phosphate buffered saline, and isotonic sodium chloride solution. In addition, sterile, fixed oils are conventionally employed as a solvent or suspending medium. For this purpose, any bland fixed mineral or non-mineral oil may be employed, including synthetic mono- or diglycerides. In addition, fatty acids such as oleic acid find use in the preparation of injectables. Carrier formulations suitable for subcutaneous, intramuscular, intraperitoneal, intravenous, etc. administrations can be found in Remington's Pharmaceutical Sciences, Mack Publishing Company, Easton, Pa.

The compounds useful in the invention can be delivered in mixtures of more than two such compounds. A mixture can further include one or more adjuvants in addition to the combination of compounds.

A variety of administration routes is available. The particular mode selected will depend, of course, upon the particular compound selected, the age and general health status of the subject, the particular condition being treated, and the dosage required for therapeutic efficacy. The methods of this invention, generally speaking, can be practiced using any mode of administration that is medically acceptable, meaning any mode that produces effective levels of response without causing clinically unacceptable adverse effects. Preferred modes of administration are discussed above.

The compositions can conveniently be presented in unit dosage form and can be prepared by any of the methods well known in the art of pharmacy. All methods include the step of bringing the compounds into association with a carrier which constitutes one or more accessory ingredients. In general, the compositions are prepared by uniformly and intimately bringing the compounds into association with a liquid carrier, a finely divided solid carrier, or both, and then, if necessary, shaping the product.

Other delivery systems can include time-release, delayed-release, or sustained-release delivery systems. Such systems can avoid repeated administrations of the compounds, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters, and fatty acids or neutral fats such as mono-, di- and triglycerides; hydrogel release systems; silastic systems; peptide-based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974, and 5,407,686. In addition, pump-based hardware delivery systems can be used, some of which are adapted for implantation.

Equivalents

The representative examples which follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art. The following examples contain important additional information, exemplification, and guidance which can be adapted to the practice of this invention in its various embodiments and equivalents thereof.

EXAMPLES

Example 1. Synthesis of Compound Formula III and Compound of Formula IIIx

Step 1: Formation of Sulfonamido-Naphthol

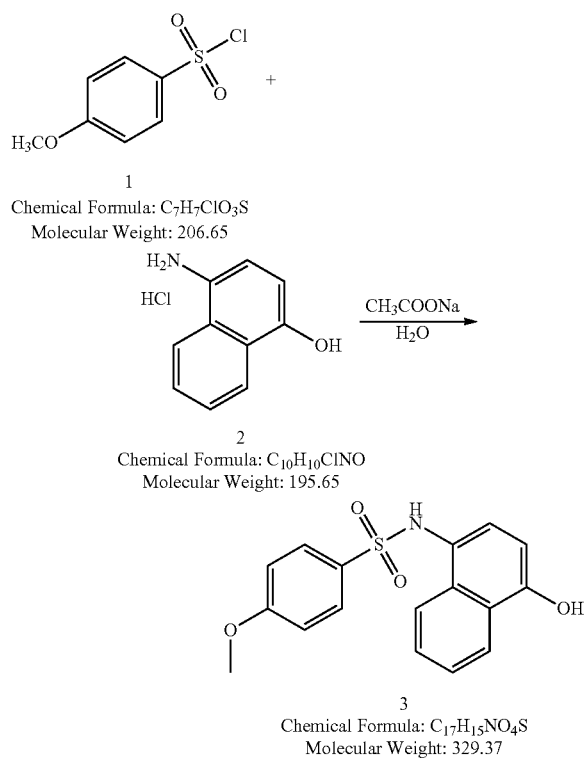

Step 1 is the reaction of 4-methoxybenzenesulfonyl chloride (1) and 4-amino-1-naphthol HCl (2) in the presence of sodium acetate to afford sulfonamido-naphthol (3). To a 5 L round bottom flask with mechanical stirring was added 2 (139.19 g, 694 mmol) and water (2.0 L). To the stirred suspension was added sodium acetate (176.12 g, 2.13 mol) and 1 (177.52 g, 816 mmol) using an additional water heel (800 mL). The reaction was heated to 85° C. via electric mantel and the temperature monitored with calibrated thermocouple. The reaction was monitored by TLC and cooled after 2 h at the set temperature. The purple precipitate formed during the reaction was filtered, washed with water (1400 mL in portions), and dried in a heated (55° C.) vacuum oven for 18 h under a nitrogen purge. The purple intermediate 3 (223.78 g, 95% yield) was characterized by 1H NMR and LCMS.

Step 2: Formation of Sulfonyl-Iminoquinone

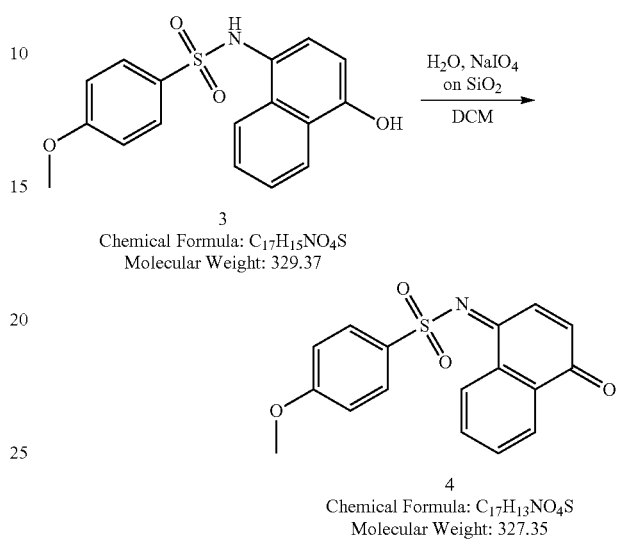

Step 2 is the oxidation of sulfonamido-naphthol (3) with sodium periodate on silica in the presence of dichloromethane (DCM) to afford sulfonyl-iminoquinone (4). Specifically, sodium periodate on silica was generated in situ by combining sodium periodate in water. A 20 L, round-bottom flask was charged with water (370 mL) and heated to 90° C. Sodium periodate (157.7 g, 737 mmol) was added with stirring and allowed to dissolve. This solution was applied by vacuum to a 20 L flask containing silica gel (624.8 g). The resulting free-flowing solids were used as is in the next step.

Intermediate 3 (120.3 g, 365 mmol) was added to a 5 L, round-bottom flask with mechanical stirring. Dichloromethane (DCM, 3 L) was added and mechanical stirring begun. To the slurry was charged the sodium periodate/silica (280.6 g, 183 mmol). The brown/yellow mixture was stirred at room temperature for 60 min, at which time TLC indicated consumption of starting material. Sodium sulfate (101 g) was added to act as a drying agent prior to filtration. The reaction was filtered and washed with DCM (680 mL), and the solution of formed intermediate 4 was transferred to a clean 5 L reactor.

Step 3: Formation of Compound of Formula IIIx

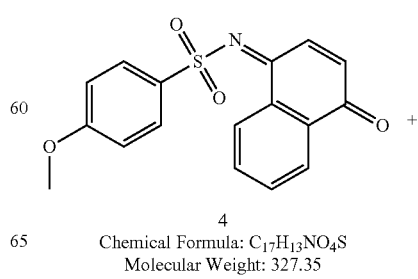

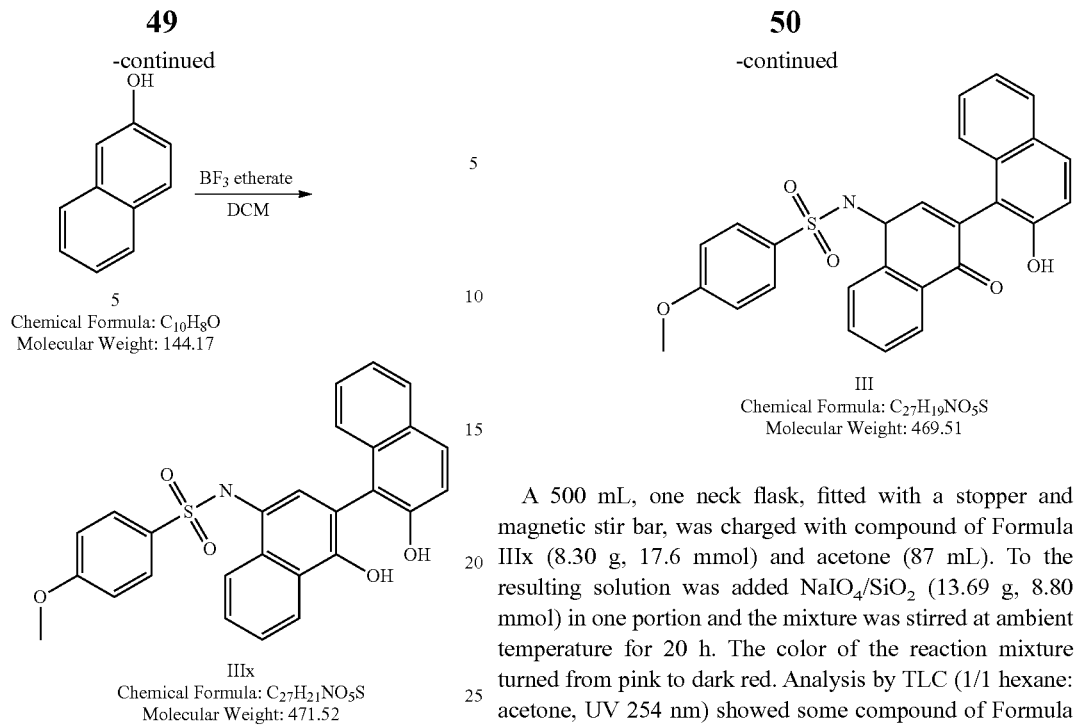

Step 3 is the in situ condensation of the sulfonyl-iminoquinone (4) with 2-naphthol (5) in the presence of dichloromethane (DCM) and catalytic boron trifluoride etherate to afford compound of Formula IIIx. The solution was blanketed with nitrogen and stirred, and 5 (52.7 g, 365 mmol) was added. Boron trifluoride etherate (2.1 mL, 17.5 mmol) was added, and the reaction was heated to 35° C. A second portion of the same quantity was added 15 min later. The reaction was stirred for 2 h, and was then filtered over a coarse frit after cooling. The product was washed with DCM (300 mL portions) in two portions. The crude product (IIIx, 154.2 g) was dried in a heated (55° C.) vacuum oven for 60 h under a nitrogen purge.

The crude compound IIx was added to a 5 L flask with absolute ethanol (1.5 L), and heated to 35° C. for 3 h. The slurry was then filtered and washed with ethanol (150 mL). The solids were dried in a heated (55° C.) vacuum oven for 24 h under a nitrogen purge. The product IIIx (143.5 g, 83% yield) was characterized by 1H NMR and LC-MS.

Step 4: Formation of Compound of Formula III

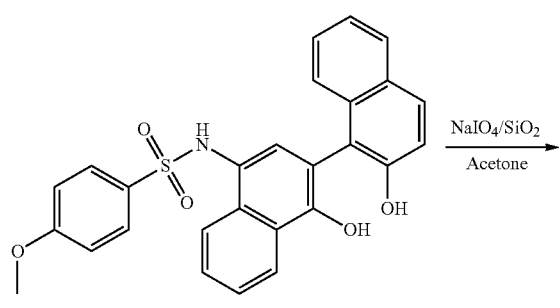

IIIx
Chemical Formula: $C_{27}H_{21}NO_5S$
Molecular Weight: 471.53

A 500 mL, one neck flask, fitted with a stopper and magnetic stir bar, was charged with compound of Formula IIIx (8.30 g, 17.6 mmol) and acetone (87 mL). To the resulting solution was added $NaIO_4/SiO_2$ (13.69 g, 8.80 mmol) in one portion and the mixture was stirred at ambient temperature for 20 h. The color of the reaction mixture turned from pink to dark red. Analysis by TLC (1/1 hexane: acetone, UV 254 nm) showed some compound of Formula IIx remaining. More $NaIO_4/SiO_2$ (13.7 g, 8.8 mmol) was added and the mixture was stirred at ambient temperature for 24 h. Analysis by TLC showed some compound of Formula IIIx remaining. The reaction mixture was filtered and the filtrate was charged with more $NaIO_4/SiO_2$ (13.7 g, 8.8 mmol). The mixture was stirred at ambient temperature for 6 h. Analysis by TLC showed some compound of Formula IIIx remaining. More $NaIO_4/SiO_2$ (13.7 g, 8.8 mmol) was added and the mixture was stirred at ambient temperature for 22 h. Analysis by TLC showed some compound of Formula IIIx remaining. The reaction mixture was filtered and more $NaIO_4/SiO_2$ (13.7 g, 8.8 mmol) was added to the filtrate. The mixture was stirred at ambient temperature for 24 h. Analysis by LC-MS showed 76% conversion to compound of Formula III. The mixture continued to stir at ambient temperature for 20 h. The reaction mixture was filtered and the flask and solids were washed with acetone. Approximately half of the filtrate was concentrated and purified by normal phase silica gel (80 g of silica, gradient 0 to 60% acetone in hexanes) to give compound of Formula III (2.3 g). IR spectrum of compound of Formula III is depicted in FIG. 1.

Example 5. STAT3 Inhibition $IC_{50}$ of Compound of Formula IIx and Compound Formula III The following compounds were tested for their ability to block STAT3 binding to its phosphopeptide ligand in a surface plasmon resonance (SPR)-based binding assay and to inhibit IL-6-mediated phosphorylation of STAT1, STAT3, and STAT5. Inhibition of nuclear translocation of phosphorylated STAT3 was also tested. The $IC_{50}$ (μM) values are shown in Table 2. More details of these assays are described in U.S. Pat. No. 8,779,001; Haricharan et al., *Mechanism and preclinical prevention of increased breast cancer risk caused by pregnancy*, Cell biology: Human biology and medicine, 2013, 1-24; the entire contents of which are incorporated by reference.

TABLE 2

| | IC$_{50}$ (µM) values of compound of Formula III | | | | | |
|---|---|---|---|---|---|---|
| Compound | | | Phosphorylation | | | |
| formula | structure | SPR | pSTAT1 | pSTAT3 | pSTAT5 | Transloc |
| Formula III | III | 2.3 | 2.2 | 3.0 | 1.8 | 18 |
| Formula IIIx | IIIx | 2.5 | 3.7 | 2.8 | 4.1 | 50 |

The invention claimed is:

1. A pharmaceutical composition, comprising
(a) a compound of Formula III,

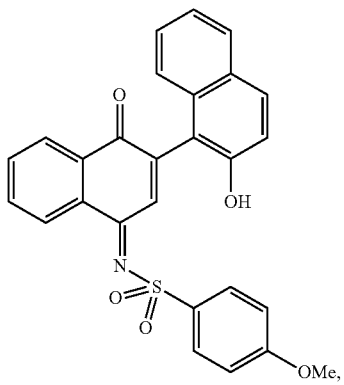

III or a pharmaceutically acceptable salt thereof, and
(b) a pharmaceutically acceptable carrier or diluent.

2. A method of treating a cancer in a subject in need thereof, the method comprising administering to the subject a therapeutically effective amount of a composition according to claim 1, wherein the cancer is selected from the group consisting of: head and neck cancer, lung cancer, liver cancer, breast cancer, ovarian cancer, colon cancer, multiple myeloma, prostate cancer, cervical cancer, brain cancer, pancreatic cancer, myelodysplastic syndrome, neuroblastoma, kidney cancer, and metastatic melanoma, wherein the compound of Formula III inhibits signal transducer and activator of transcription 3 (STAT3) thereby treating the cancer in the subject.

3. The method of claim 2, wherein the cancer is selected from the group consisting of head and neck cancer, lung cancer, liver cancer, breast cancer, ovarian cancer, colon cancer, multiple myeloma, and pancreatic cancer.

4. A method of treating fibrosis in a subject in need thereof, the method comprising administering to the subject a therapeutically effective amount of a composition according to claim 1, wherein the compound of Formula III inhibits signal transducer and activator of transcription 3 (STAT3) thereby treating the fibrosis in the subject.

5. The method of claim 4, wherein the fibrosis is associated with a disease or disorder selected from the group consisting of: pulmonary fibrosis, intestine fibrosis, pancreatic fibrosis, joint fibrosis, liver fibrosis, retroperitoneal fibrosis, myelofibrosis, dermal fibrosis, non-alcoholic fatty liver disease, steatohepatitis, and systemic sclerosis.

6. The method of claim 4, wherein the fibrosis is associated with pulmonary fibrosis, non-alcoholic fatty liver disease, steatohepatitis, or systemic sclerosis.

\* \* \* \* \*